US012569244B2

(12) United States Patent
Khanicheh et al.

(10) Patent No.: US 12,569,244 B2
(45) Date of Patent: Mar. 10, 2026

(54) ENDOSCOPIC SUTURE CUTTER

(71) Applicant: EnVision Endoscopy, Inc., Waltham, MA (US)

(72) Inventors: Azadeh Khanicheh, Somerville, MA (US); Amos G. Cruz, Wrentham, MA (US); Judy Walish, Boston, MA (US); William Zouzas, Waltham, MA (US)

(73) Assignee: EnVision Endoscopy, Inc., Waltham, MA (US)

( * ) Notice: Subject to any disclaimer, the term of this patent is extended or adjusted under 35 U.S.C. 154(b) by 201 days.

(21) Appl. No.: 18/236,902

(22) Filed: Aug. 22, 2023

(65) Prior Publication Data

US 2024/0057993 A1 Feb. 22, 2024

Related U.S. Application Data

(60) Provisional application No. 63/399,987, filed on Aug. 22, 2022.

(51) Int. Cl.
*A61B 17/04* (2006.01)

(52) U.S. Cl.
CPC ...... *A61B 17/0467* (2013.01); *A61B 17/0469* (2013.01)

(58) Field of Classification Search
CPC . A61B 17/0467; A61B 17/0469; A61B 17/32; A61B 17/32002; A61B 17/320036; A61B 1/00131
See application file for complete search history.

(56) References Cited

U.S. PATENT DOCUMENTS

| | | | | |
|---|---|---|---|---|
| 3,995,619 | A | 12/1976 | Glatzer | |
| 4,765,332 | A * | 8/1988 | Fischell | A61B 17/32075 606/159 |
| 5,366,459 | A * | 11/1994 | Yoon | A61B 17/0057 606/151 |
| 5,624,455 | A * | 4/1997 | Matsuno | A61B 17/32075 606/171 |
| 5,658,302 | A * | 8/1997 | Wicherski | A61B 17/32075 606/159 |
| 7,651,503 | B1 * | 1/2010 | Coe | A61N 1/056 606/108 |
| 9,782,191 | B2 * | 10/2017 | Krieger | B21F 45/008 |
| 2002/0087178 | A1 * | 7/2002 | Nobles | A61B 17/0469 606/167 |
| 2005/0234481 | A1 * | 10/2005 | Waller | A61B 17/0467 606/148 |
| 2007/0106310 | A1 | 5/2007 | Goldin et al. | |
| 2009/0259234 | A1 | 10/2009 | Waller | |

(Continued)

OTHER PUBLICATIONS

International Search Report and Written Opinion for International Application No. PCT/US2023/030870, mailed Dec. 11, 2023, 11 pages.

*Primary Examiner* — Phong Son H Dang
(74) *Attorney, Agent, or Firm* — Nutter McClennen & Fish LLP

(57) ABSTRACT

A method is used to cut a suture. The method provides a drive wire coupled with a cutter. The cutter has a first blade defining a first plane, and a second blade defining a second plane that is non-parallel with the first plane. The first blade and the second blade define an opening. The method hooks a suture into the opening. The method cuts the suture by pulling the drive wire in a proximal direction.

17 Claims, 27 Drawing Sheets

(56)                    References Cited

U.S. PATENT DOCUMENTS

| | | | |
|---|---|---|---|
| 2010/0286719 A1 * | 11/2010 | Paul | A61B 17/3207 |
| | | | 606/159 |
| 2014/0046140 A1 | 2/2014 | Abuhamad | |
| 2015/0201958 A1 | 7/2015 | Krieger et al. | |
| 2021/0113232 A1 | 4/2021 | Ortiz Garcia et al. | |
| 2021/0322004 A1 | 10/2021 | Khanicheh et al. | |
| 2022/0233182 A1 | 7/2022 | Ostrovsky et al. | |
| 2022/0257236 A9 | 8/2022 | Khanicheh et al. | |
| 2022/0387017 A1 | 12/2022 | Walish et al. | |
| 2023/0102138 A1 * | 3/2023 | Shuey | A61B 17/0467 |
| | | | 606/139 |
| 2023/0110619 A1 | 4/2023 | Khanicheh et al. | |
| 2023/0116167 A1 | 4/2023 | Khanicheh et al. | |
| 2025/0176958 A1 * | 6/2025 | Choi | A61B 17/0469 |

* cited by examiner

*FIG. 3C*
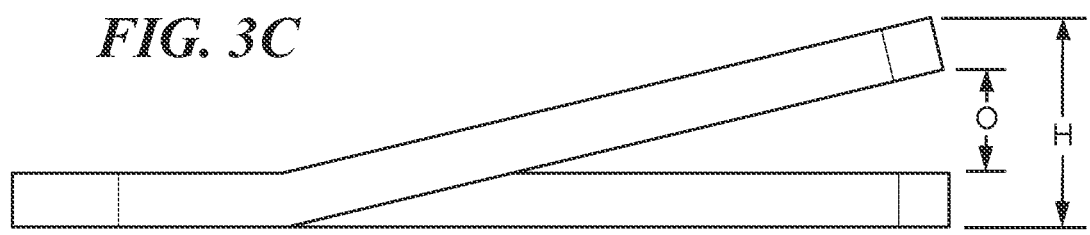
*FIG. 3D*
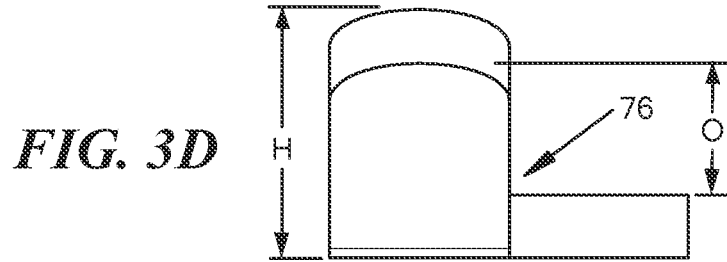
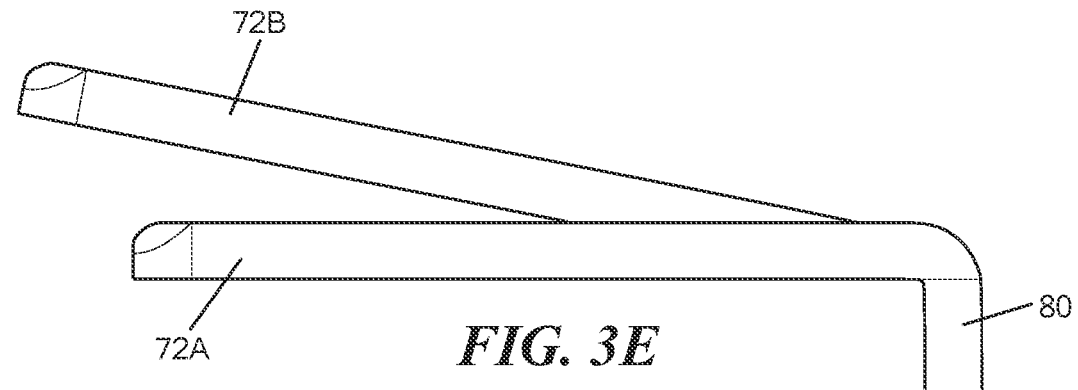
*FIG. 3E*
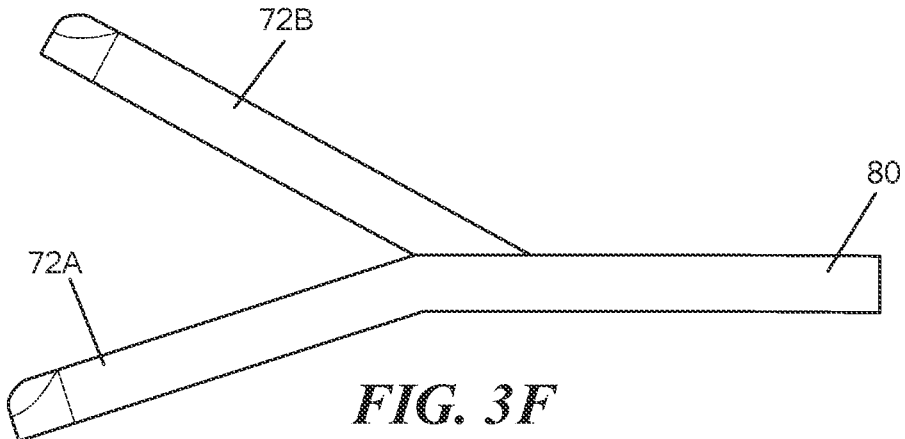
*FIG. 3F*

ENDOSCOPIC SUTURE CUTTER

PRIORITY

This patent application claims priority from provisional U.S. patent application No. 63/399,987, filed Aug. 22, 2022, the disclosure of which is incorporated herein, in its entirety, by reference.

FIELD OF THE INVENTION

Illustrative embodiments of the invention generally relate to endoscopic devices and, more particularly, the various embodiments of the invention relate to a suture cutter that is delivered through a working channel of the endoscope.

BACKGROUND OF THE INVENTION

After an endoscopic surgical procedure, sutures are often used to secure a perforation or wound closed and to promote healing. Certain types of sutures, such as absorbable sutures, are left to disintegrate over time and other types of sutures, such as non-absorbable sutures, require removal at a later date. For example, sutures requiring removal include mono-filament or braided sutures made of polyester, polypropylene or coated with plastic.

Endoscopic scissors are a type of surgical scissor used in endoscopic and laparoscopic medical procedures for dissecting tissue and sutures. Endoscopic scissors are available in many blade configurations, including bent, curved, hooked, large, small, and straight to give the surgeon a wide range of options to choose from when planning a surgical cutting strategy. The traditional "Mayo" scissors are heavy-duty scissors and the "Metzenbaum" scissors are smaller, finer-edged scissors, designed for open procedures.

SUMMARY OF VARIOUS EMBODIMENTS

In accordance with one embodiment of the invention, a method cuts a suture. The method positions a flexible insertion tube of an endoscope inside of a patient. A cutter that is coupled with a drive wire is moved through a working channel of the flexible insertion tube. The drive wire is configured to move the cutter along a central axis of the working channel. The cutter has a proximally-facing suture receiving portion leading to a sharp edge. The method extends the cutter out of the working channel of the insertion tube. A suture is positioned adjacent to the sharp edge. The suture is then cut by pulling the drive wire proximally.

Pulling the drive wire proximally applies tension to the suture using the cutter, particularly one or more sharp edges of the cutter. To positioning the suture adjacent to the sharp edge, the method may pass the suture through the suture receiving portion. To that end, the suture receiving portion may be positioned distally of a portion of the suture. A portion of the suture may be aligned with the suture receiving portion. The suture receiving portion is then moved proximally to receive the aligned portion of the suture within the suture receiving portion.

The method may be repeated. For example, the sharp edge may be positioned adjacent to a second suture. The second suture may be cut by pulling the cutter proximally. In various embodiments, the flexible insertion tube may be angulated as the cutter moves through it. In particular, the flexible insertion tube may be angulated near the distal end. For ease of moving through the insertion tube, the cutter may have a rigid longitudinal traversal length L of less than about 8 mm, preferably less than 5 mm. In some embodiments, the cutter may have a rigid longitudinal traversal length L of greater than about 0.9 mm.

In various embodiments, the cutter may be retracted into the working channel and/or a delivery shaft or the cutting device. The drive wire may be coupled with a retraction feature that is configured to position and orient the cutter to reduce or prevent interference with the delivery shaft. In various embodiments, the drive ware may be coupled with an inner surface of the retraction feature. The retraction feature may include, among other things, a hypodermic tube. The hypodermic tube may be sized to be less than the size of the inner diameter of the delivery shaft.

In accordance with another embodiment, a suture cutting device includes a drive wire coupled with a cutter. The cutter has a first blade defining a first plane, and a second blade defining a second plane that is non-parallel with the first plane.

The first blade and the second blade are non-moving. Furthermore, the first blade and the second blade may define a suture receiving portion. The drive wire has a proximal end and a distal end, and the suture receiving portion may face substantially towards the proximal end. Additionally, the first blade and the second blade may provide a passive cutting mechanism.

In accordance with another embodiment, a method cuts a suture. The method provides a drive wire coupled with a cutter. The cutter has a first blade defining a first plane, and a second blade defining a second plane that is non-parallel with the first plane. The first blade and the second blade define an opening. The method hooks a suture into the opening. The method cuts the suture by pulling the drive wire in a proximal direction.

In some embodiments, the cutter may face in a substantially distally-facing direction. In particular, some embodiments may have the suture receiving portion facing distally. Accordingly, some embodiments may simply push the cutter towards the suture to cut the suture. Of course, some other embodiments may position the cutter in a proximally-facing direction, such that the cutter may be pulled to cut the suture.

In accordance with yet another embodiment, a suture cutting system includes an endoscope having an insertion tube. The insertion tube has at least one working channel. The system includes a cutting device. The cutting device includes a handle movably coupled with a flexible drive wire. The handle is configured to move the drive wire proximally or distally within a working channel of an endoscope. A cutter is coupled with a distal end of the drive wire. Movement of the drive wire in a distal direction causes movement of cutter in a distal direction. The cutter has a rigid longitudinal traversal length L of less than about 8 mm.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

3

Figure 2A:
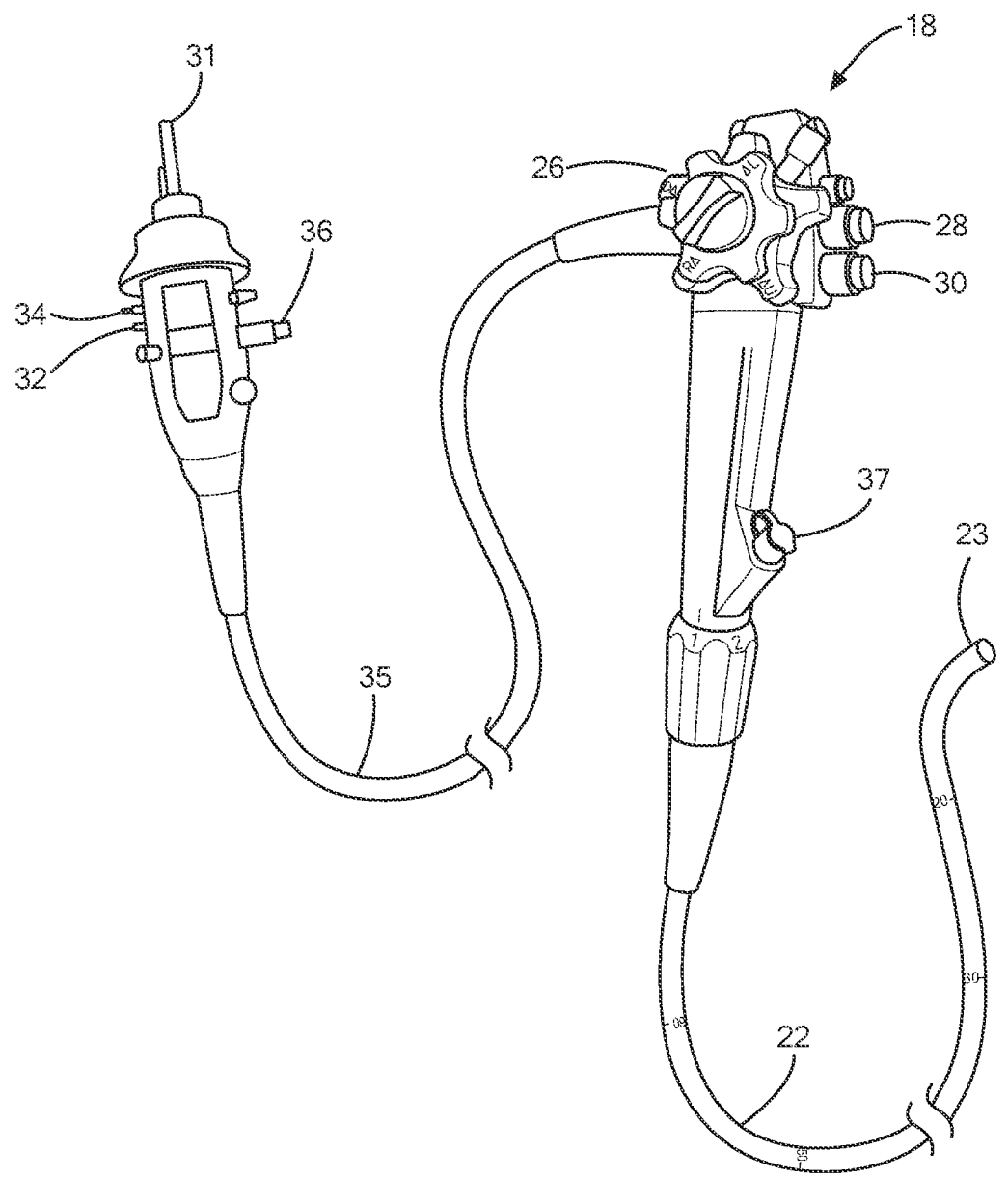
FIG. 2A schematically shows an endoscope in accordance with illustrative embodiments of the invention.
Figures 2B, 2C:
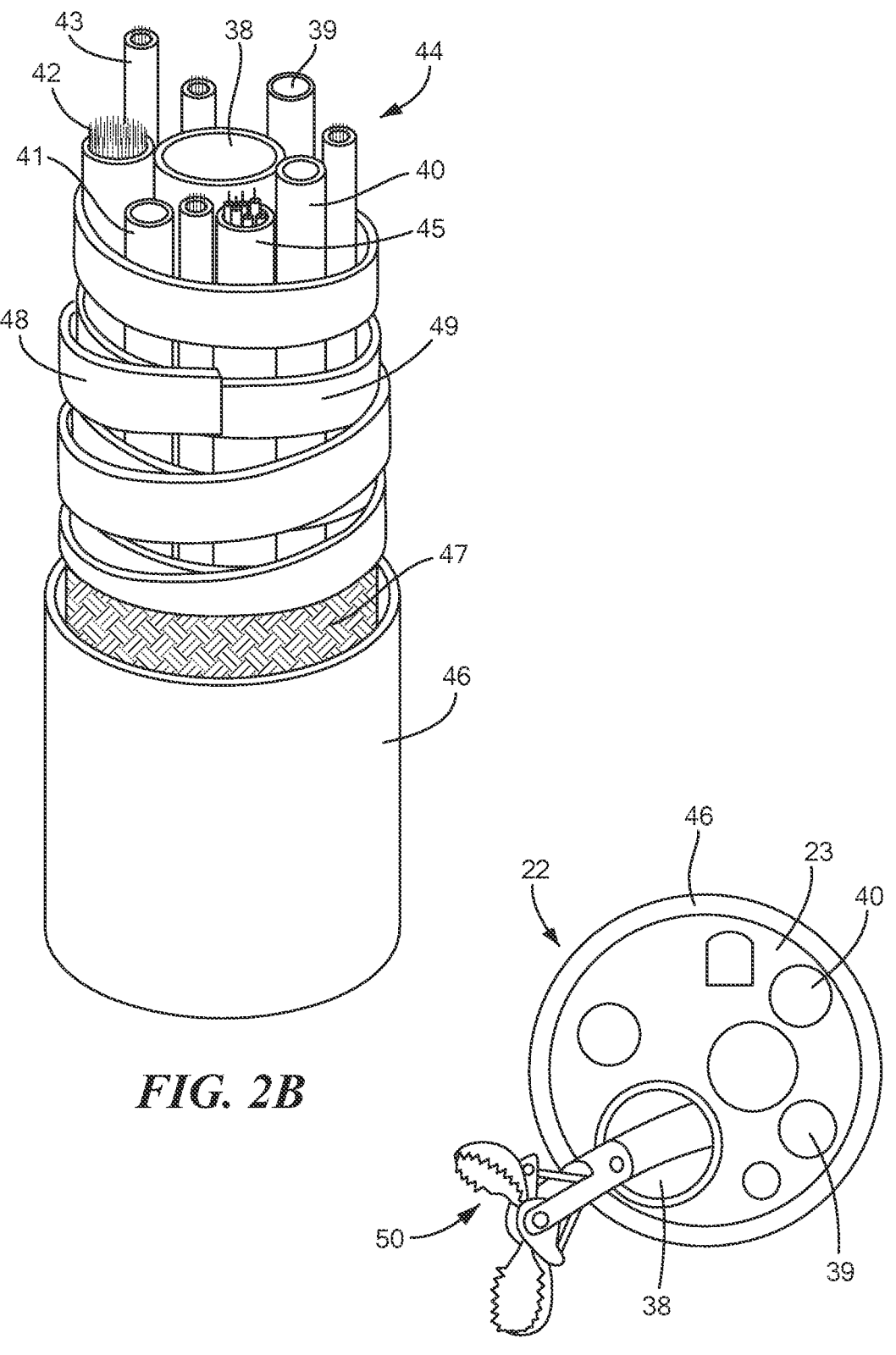
FIG. 2B schematically shows a partially exposed view of the insertion tube in accordance with illustrative embodiments.

FIG. 2C schematically shows the distal end of the insertion tube in accordance with illustrative embodiments of the invention.

Figure 2D:
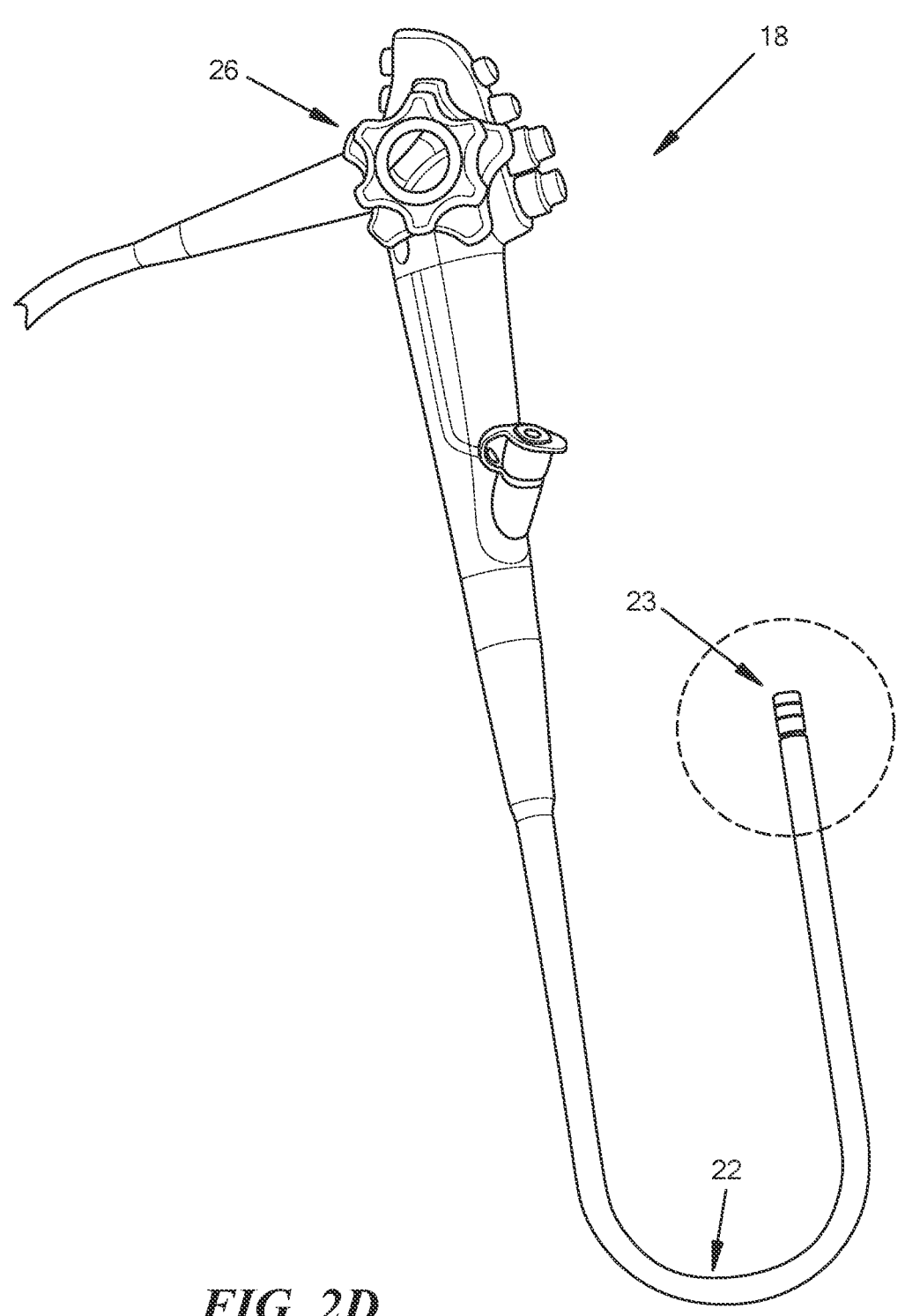

FIG. 2D schematically shows the endoscope of FIG. 2A with the insertion tube straight at the distal end.

Figure 2E:
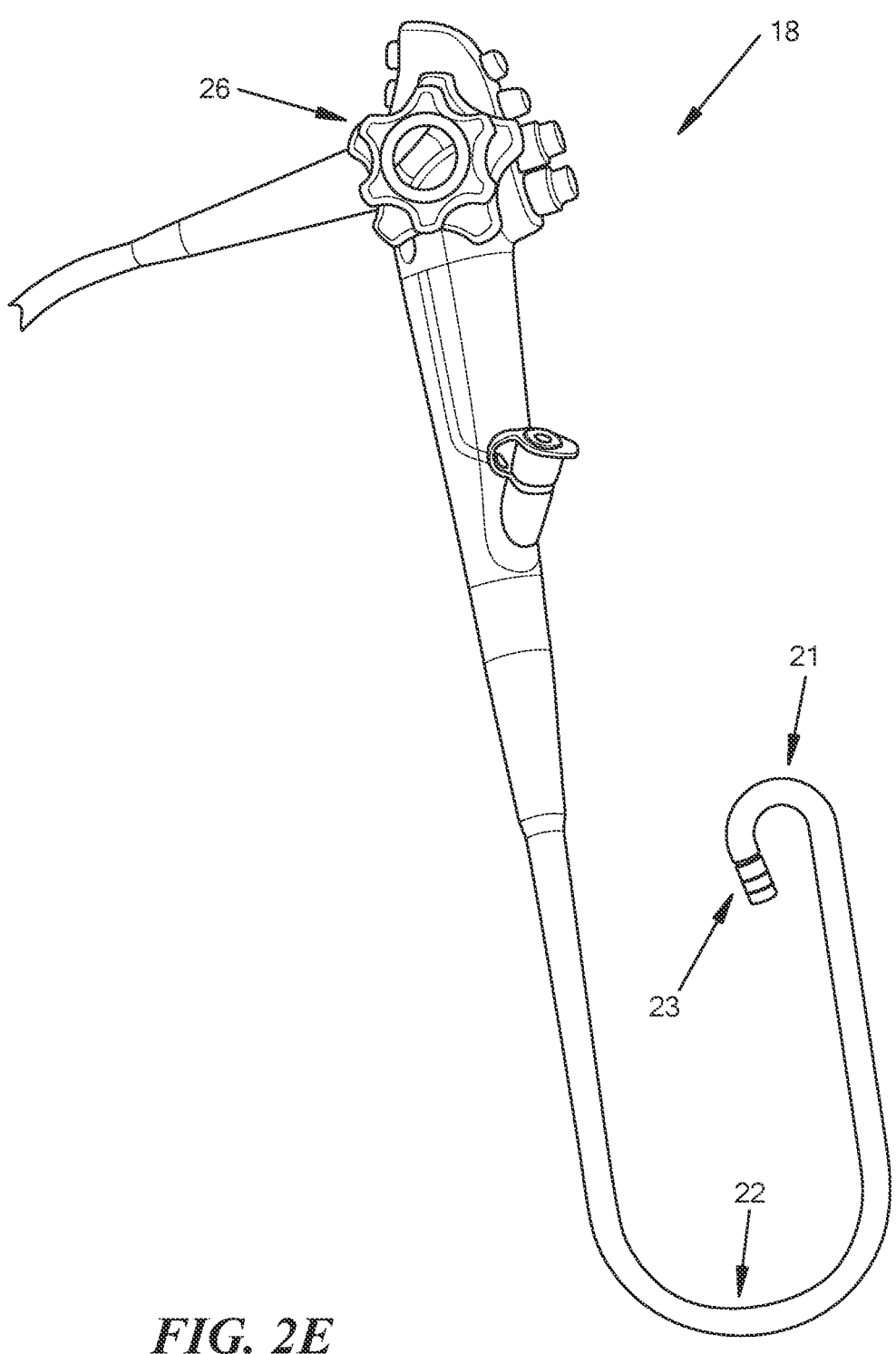

FIG. 2E schematically shows the endoscope of FIG. 2A with the insertion tube angulated near the distal end.

Figure 2F:
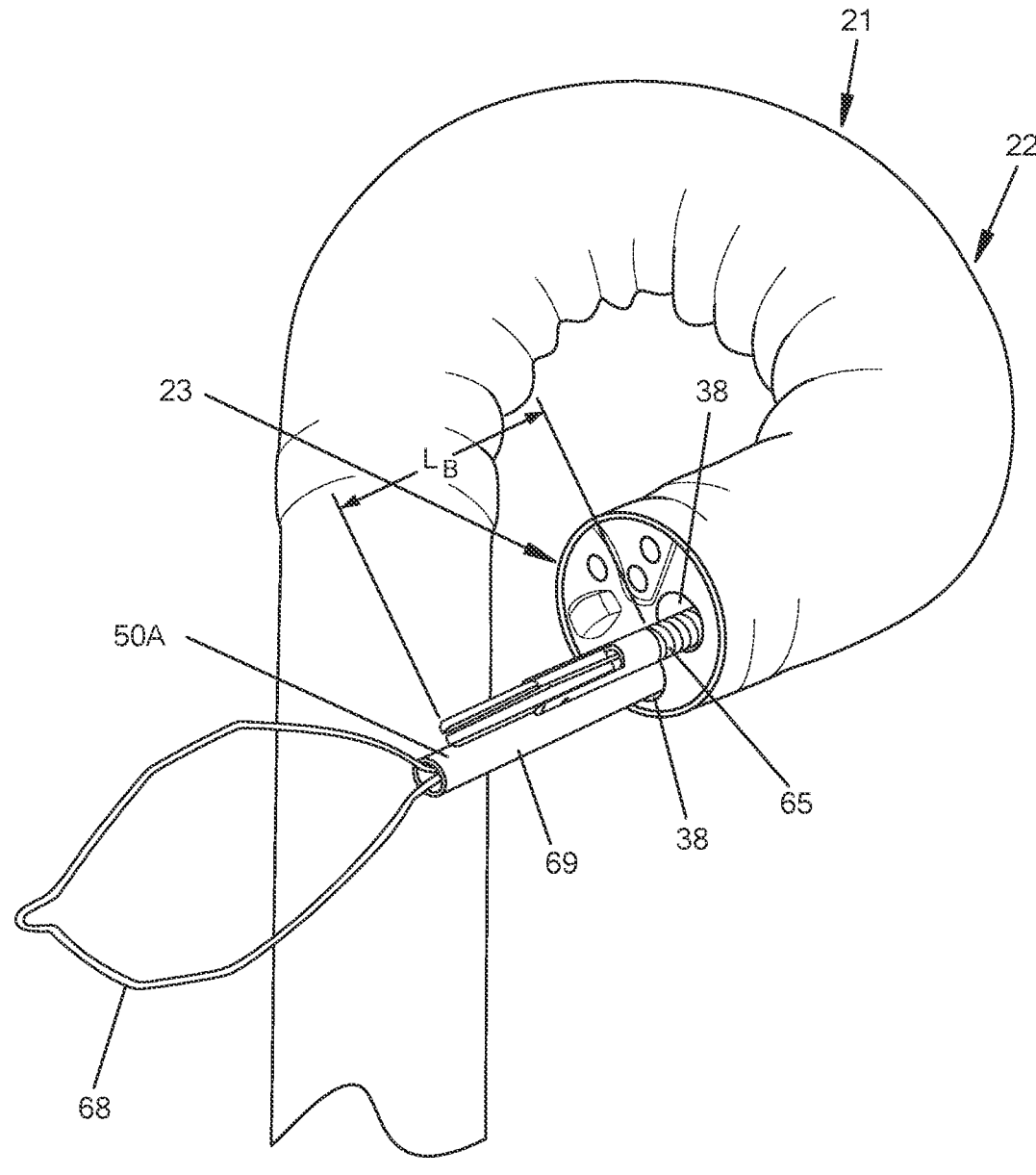

FIG. 2F schematically shows the endoscope of FIG. 2A with a curved insertion tube near the distal end.

Figure 3A:
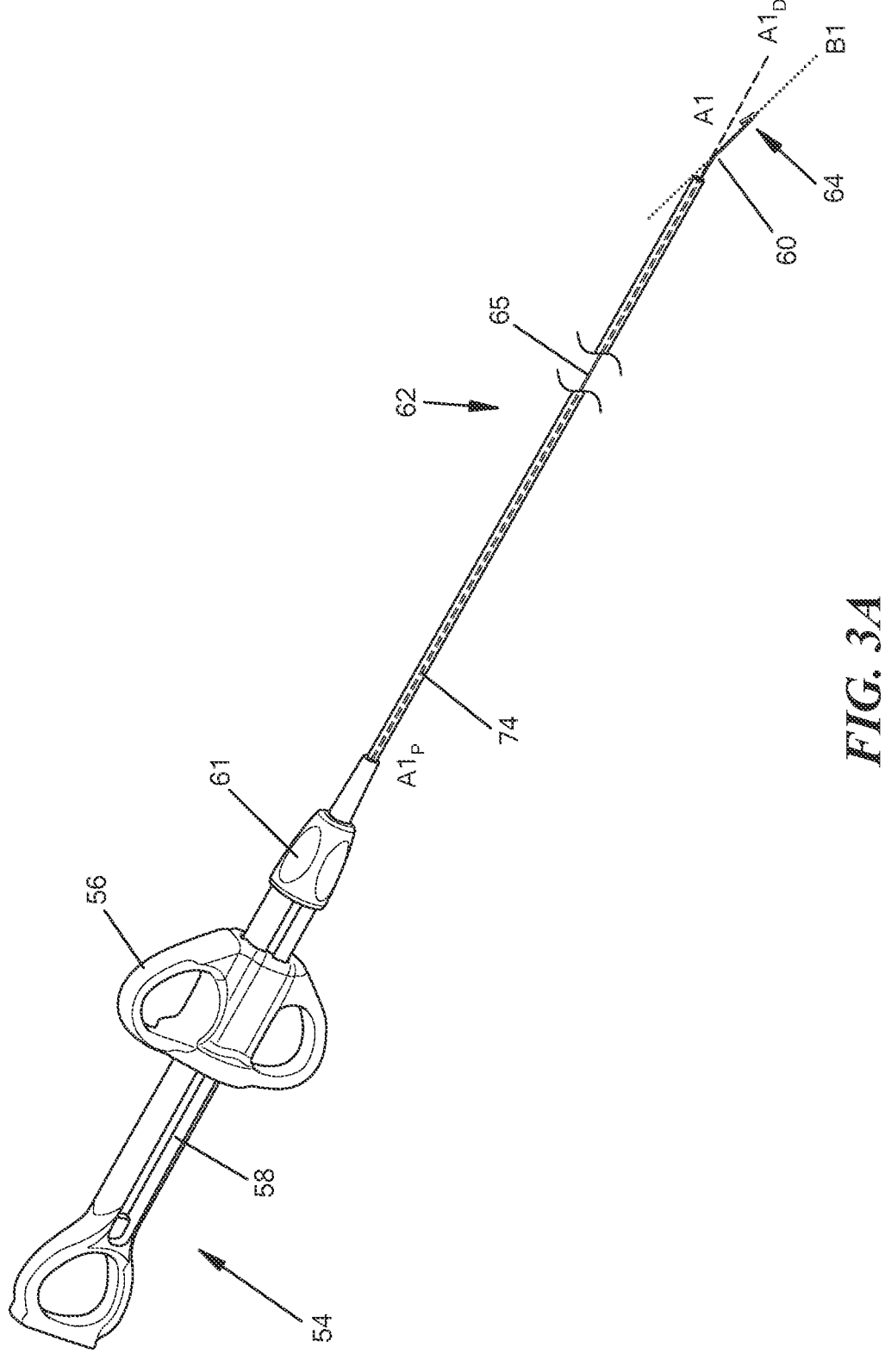

FIG. 3A schematically shows a cutting device in accordance with illustrative embodiments.

Figure 3B:
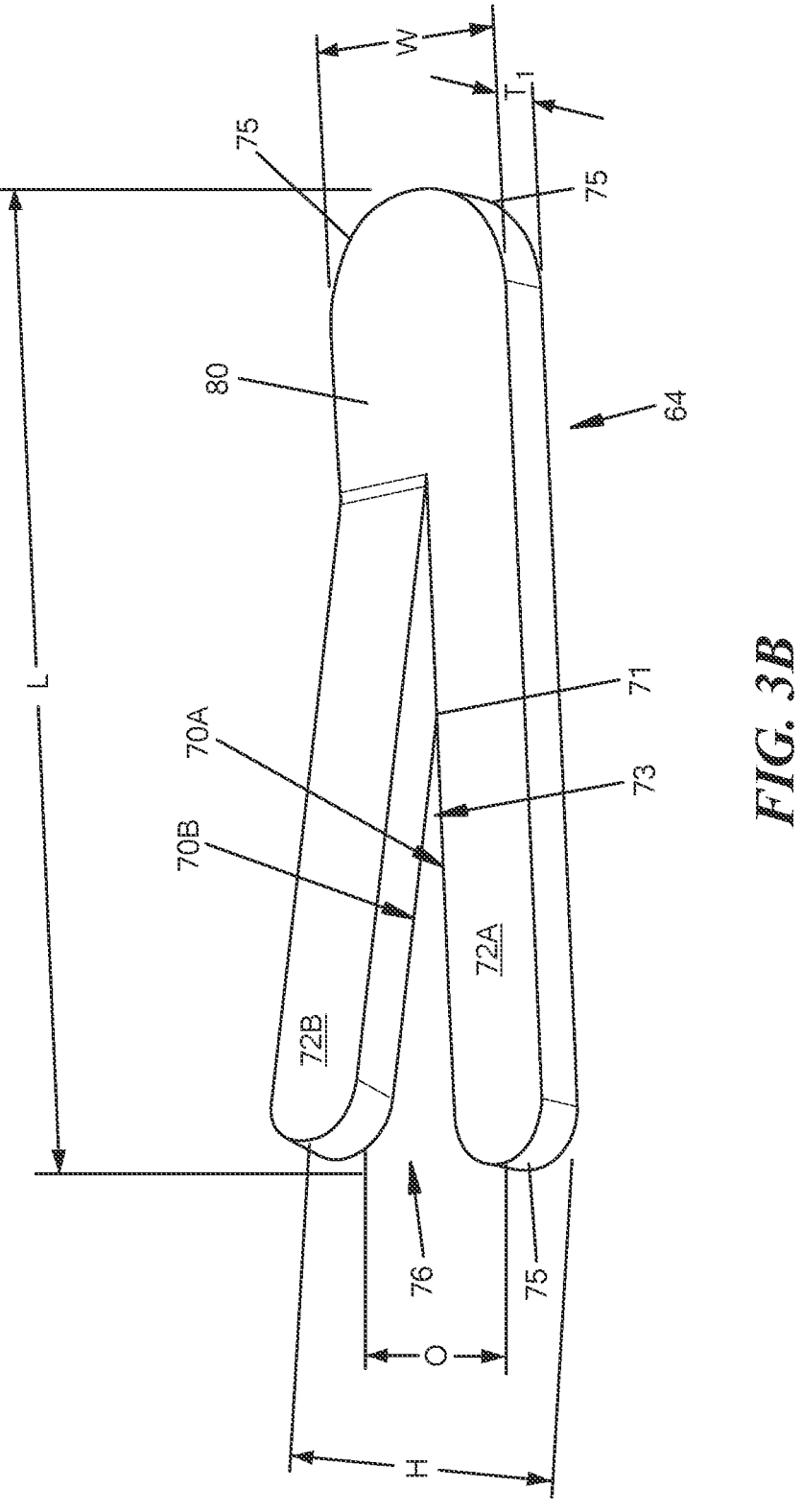
Figure 4:
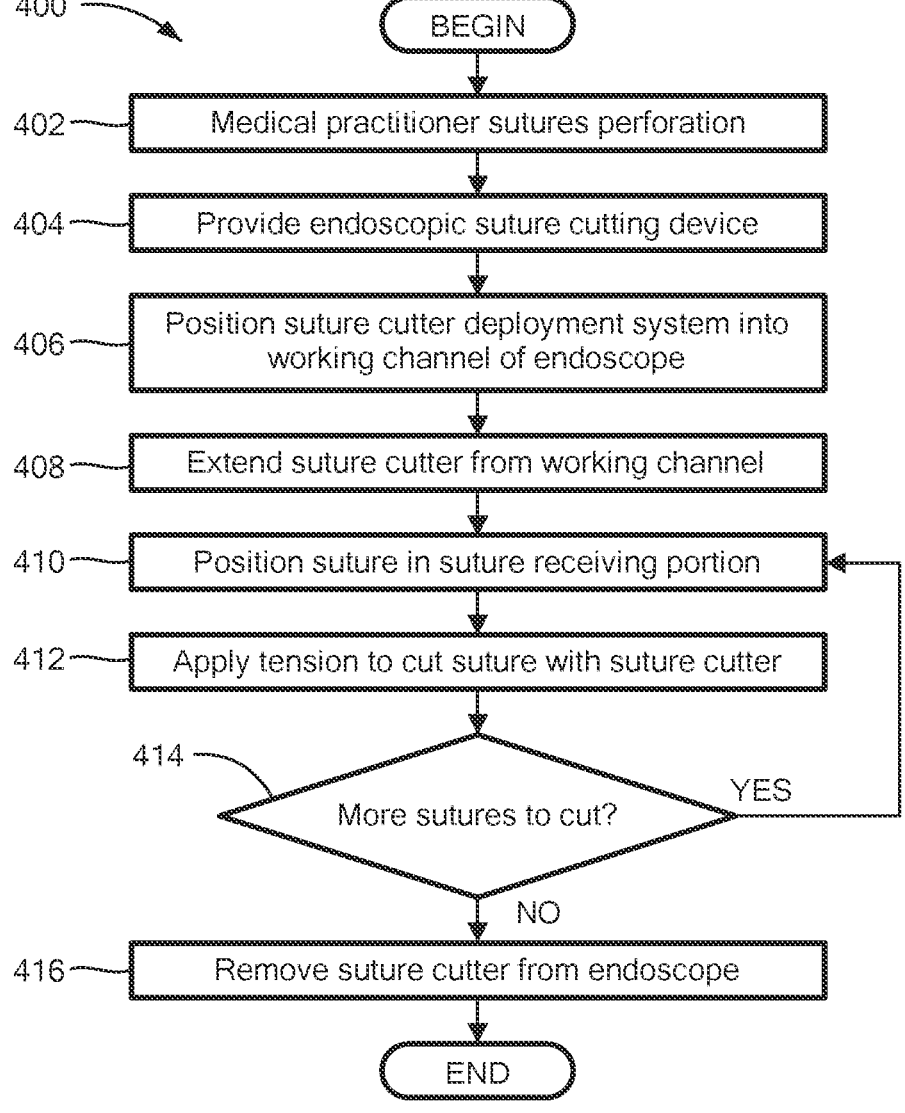

FIGS. 3B-3F schematically show detailed views of the cutter in accordance with illustrative embodiments of the invention FIG. 4 shows a process of cutting a suture in accordance with illustrative embodiments of the invention.

Figure 5:
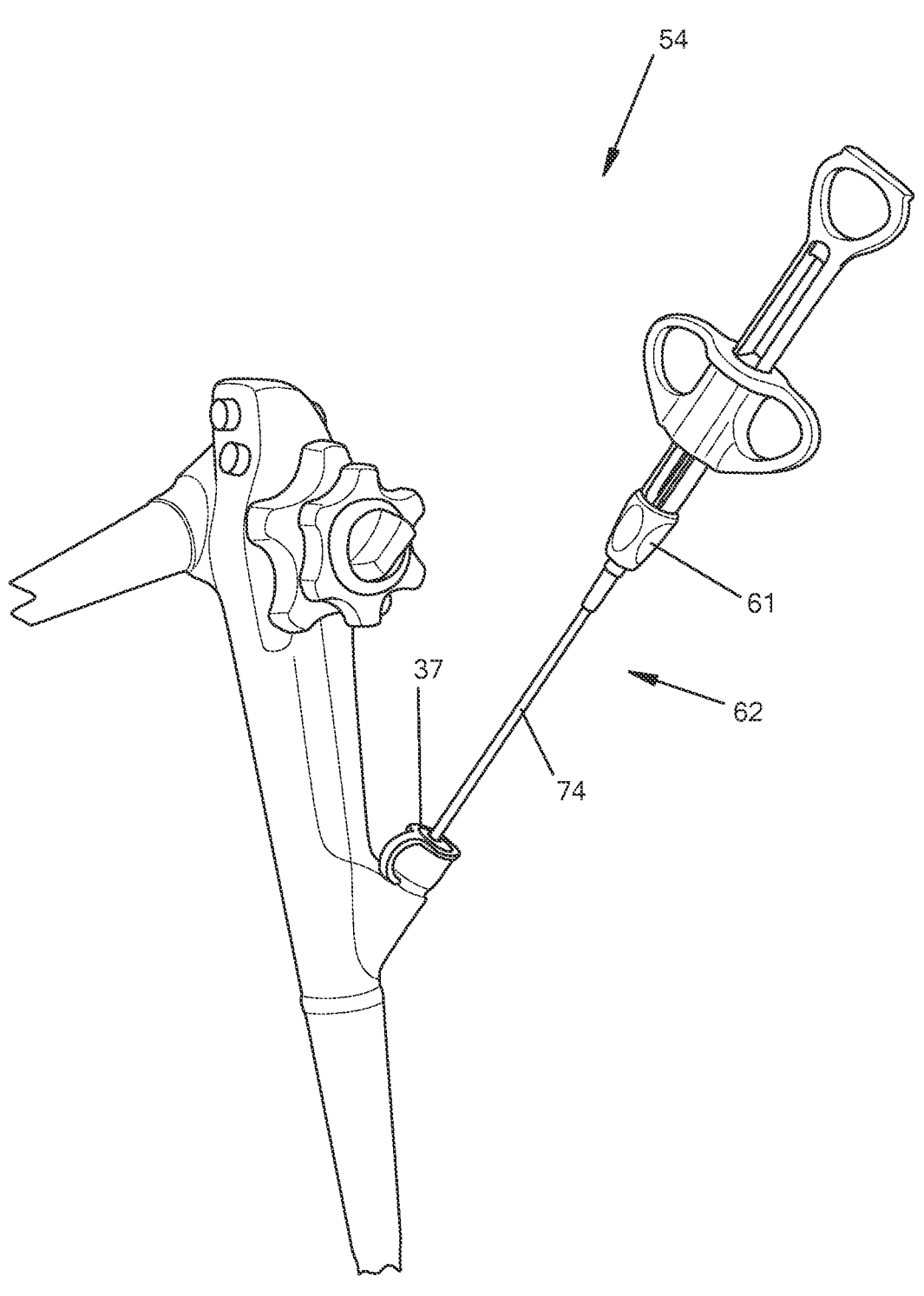

FIG. 5 schematically shows the delivery shaft positioned in the accessory port in accordance with illustrative embodiments of the invention.

Figures 6A, 6B:
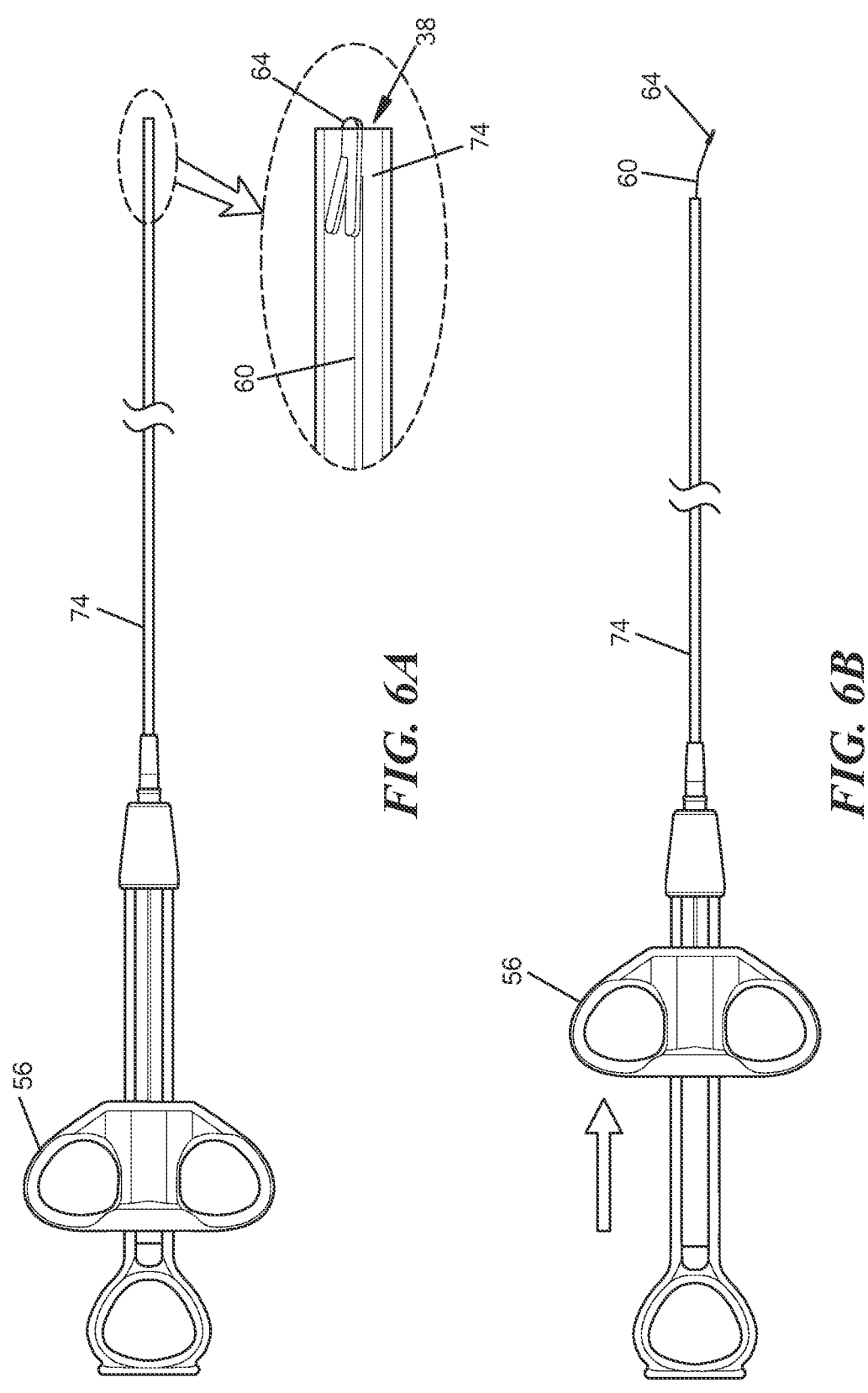

FIGS. 6A-6B schematically shows the suture cutter transitioning from being inside the delivery shaft to extending outside of the delivery shaft in accordance with illustrative embodiments of the invention.

Figure 7:
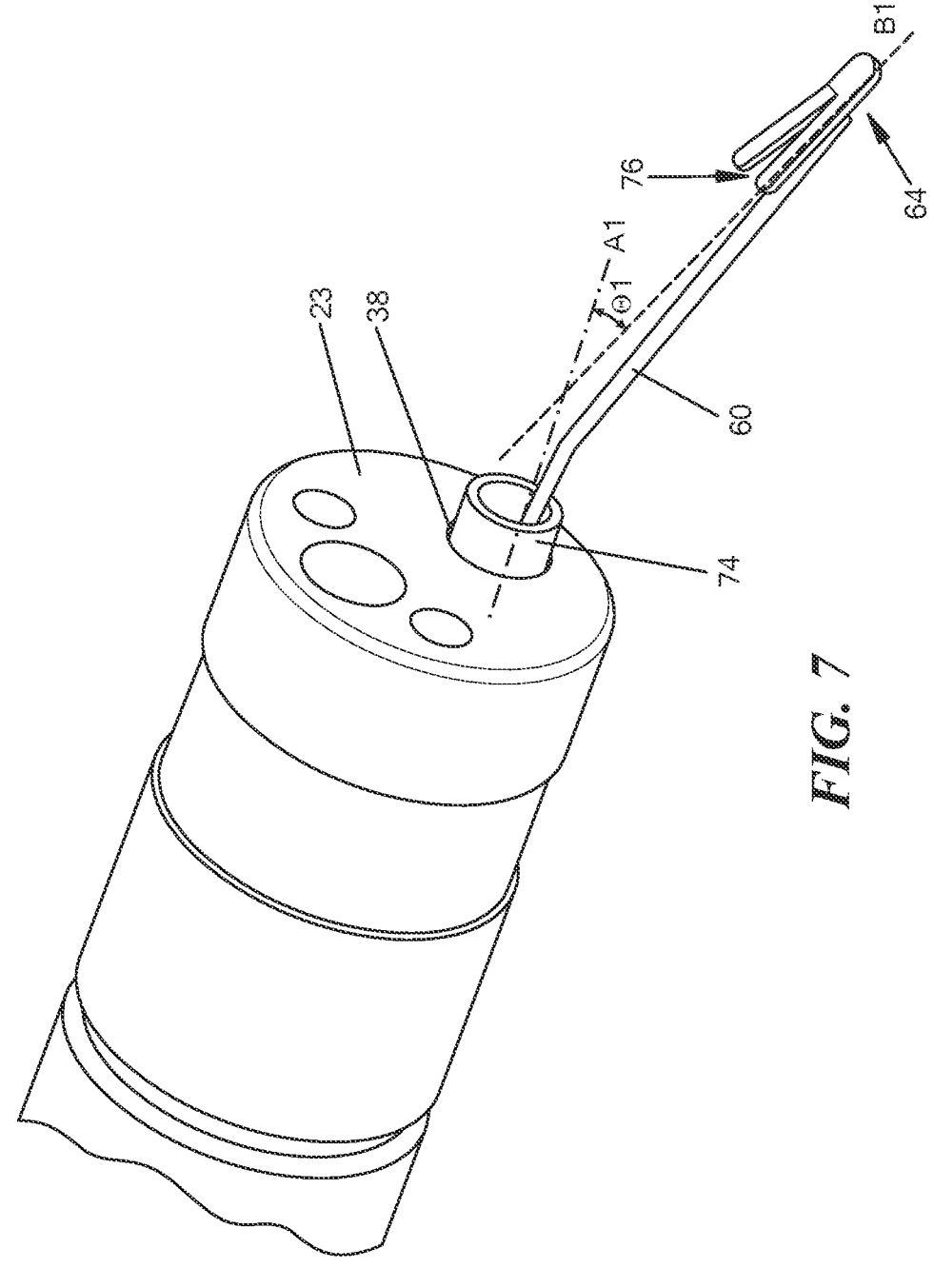

FIG. 7 shows a perspective view of the suture cutter extended from the working channel of the endoscope in accordance with illustrative embodiments of the invention.

Figure 8A:
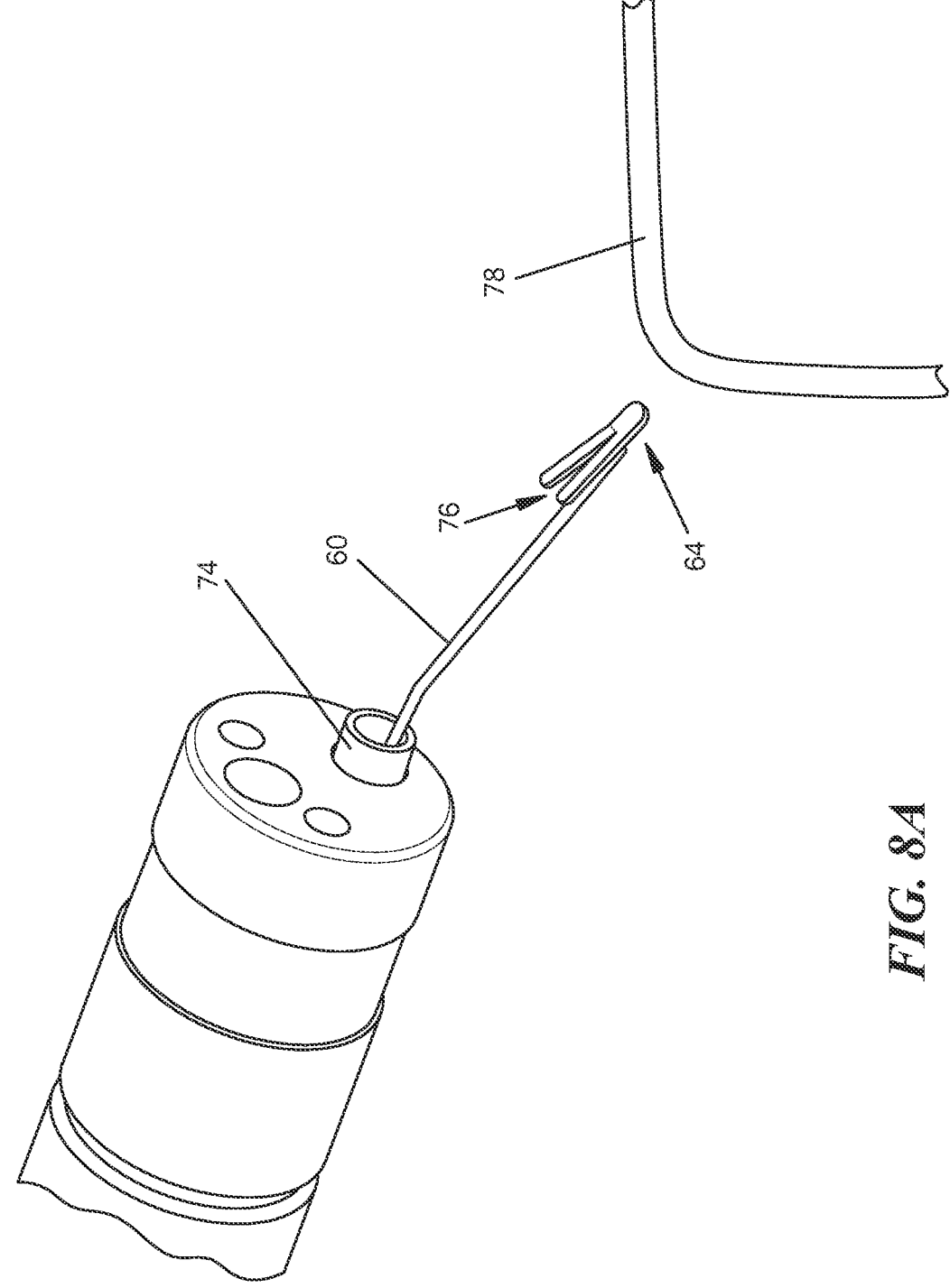
Figure 8B:
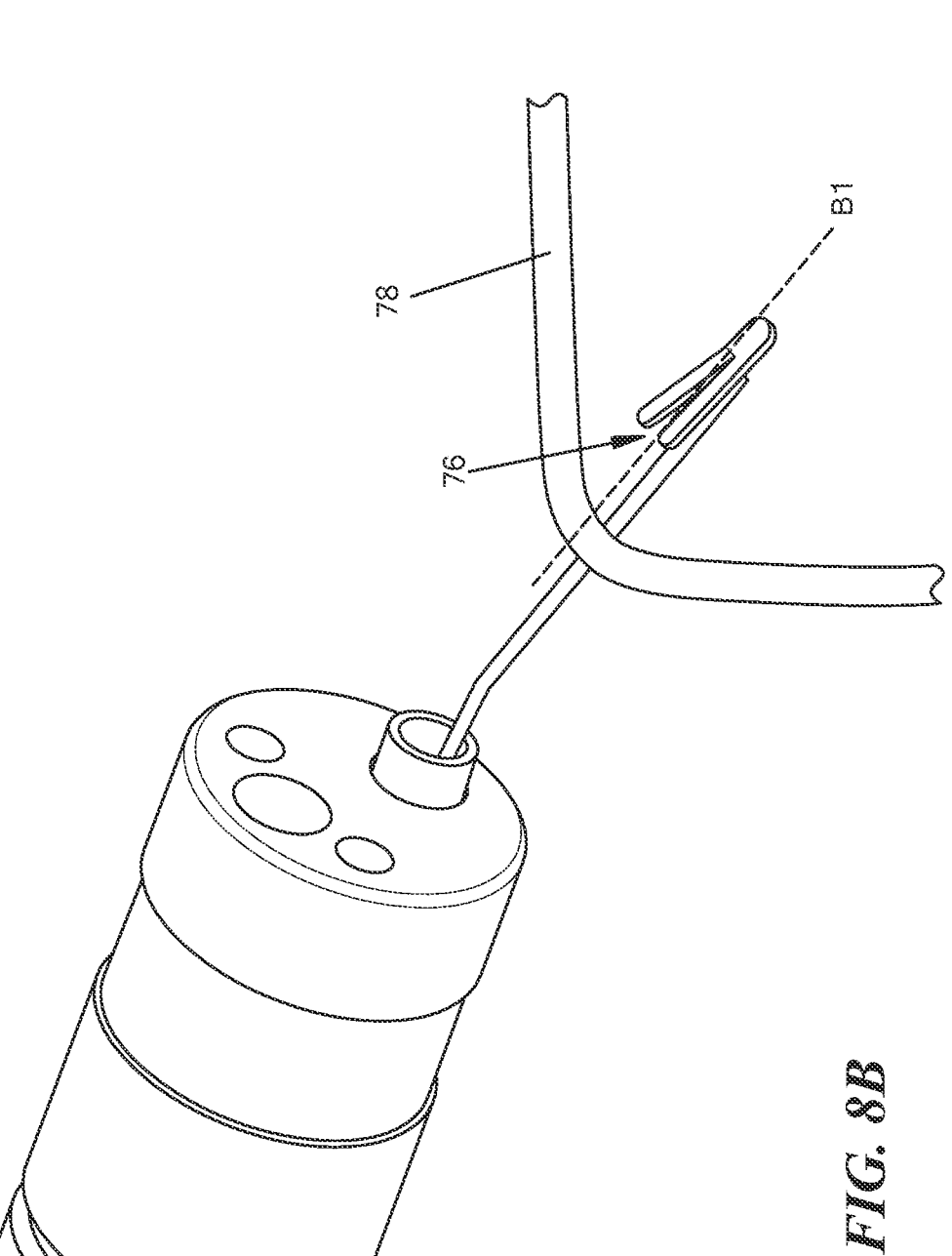
Figure 8C:
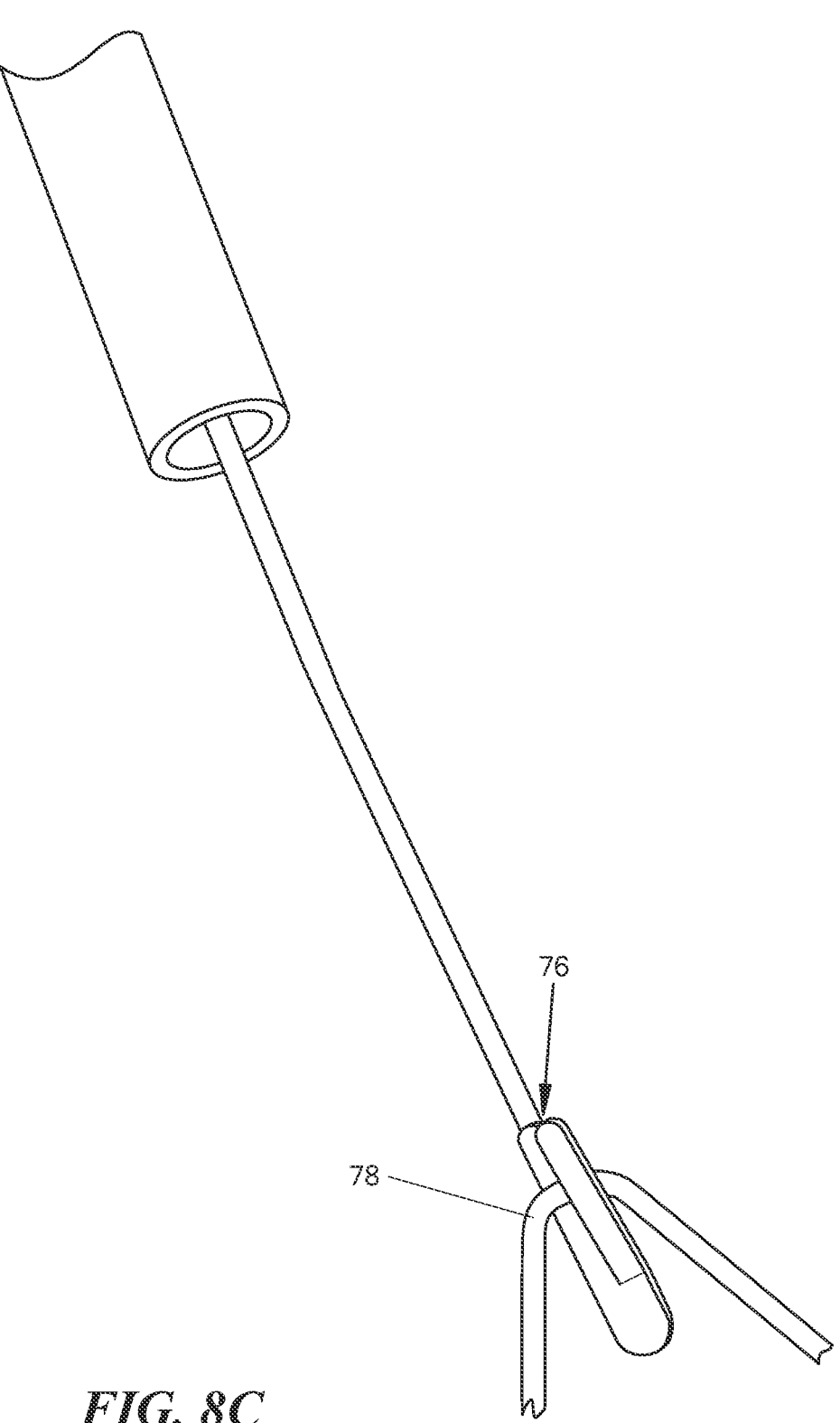

FIGS. 8A-8C schematically show the suture being positioned in the suture receiving portion in accordance with illustrative embodiments of the invention.

Figure 9:
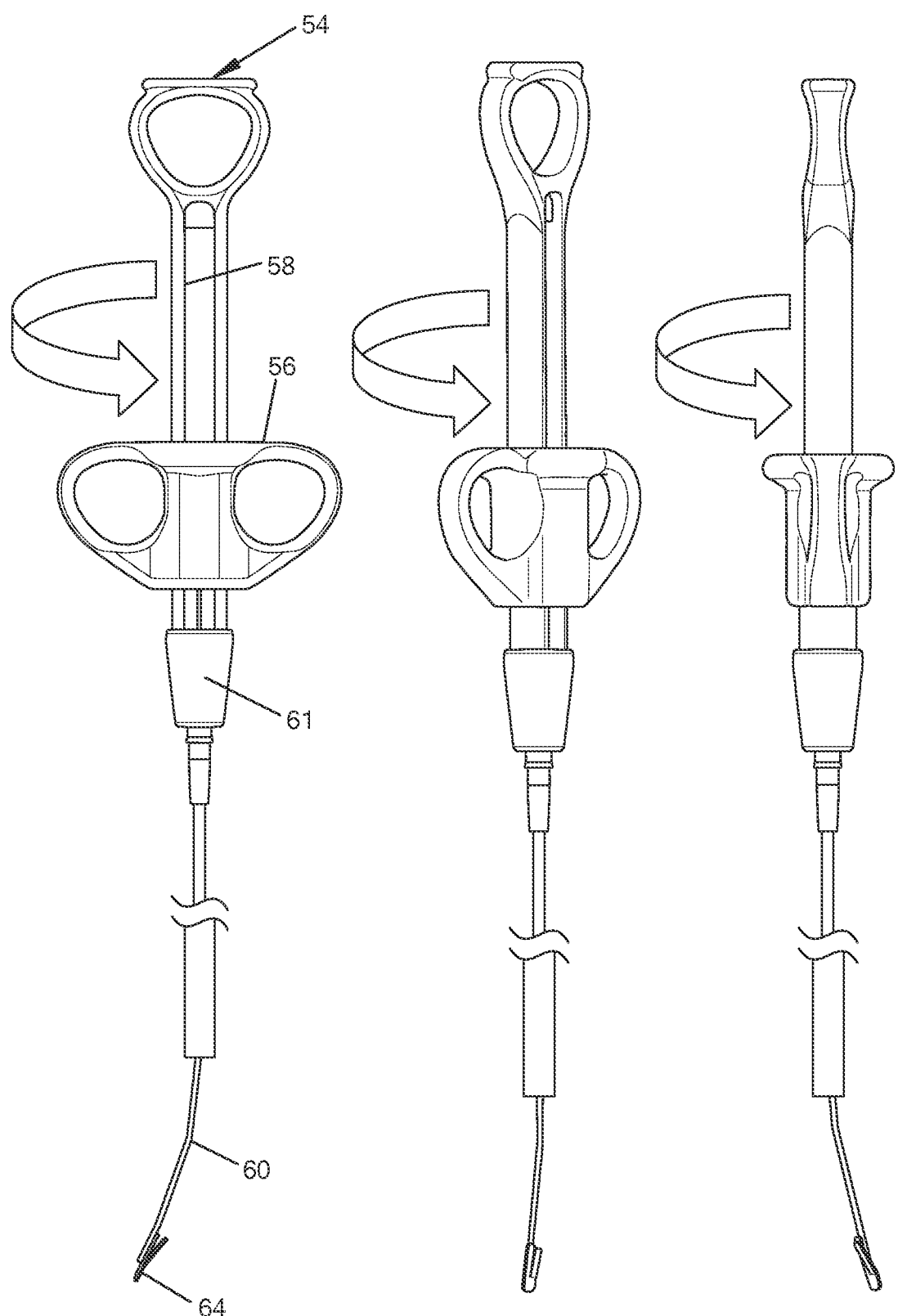

FIG. 9 schematically show a rotation feature of the cutting device in accordance with illustrative embodiments of the invention.

Figures 10A, 10B:
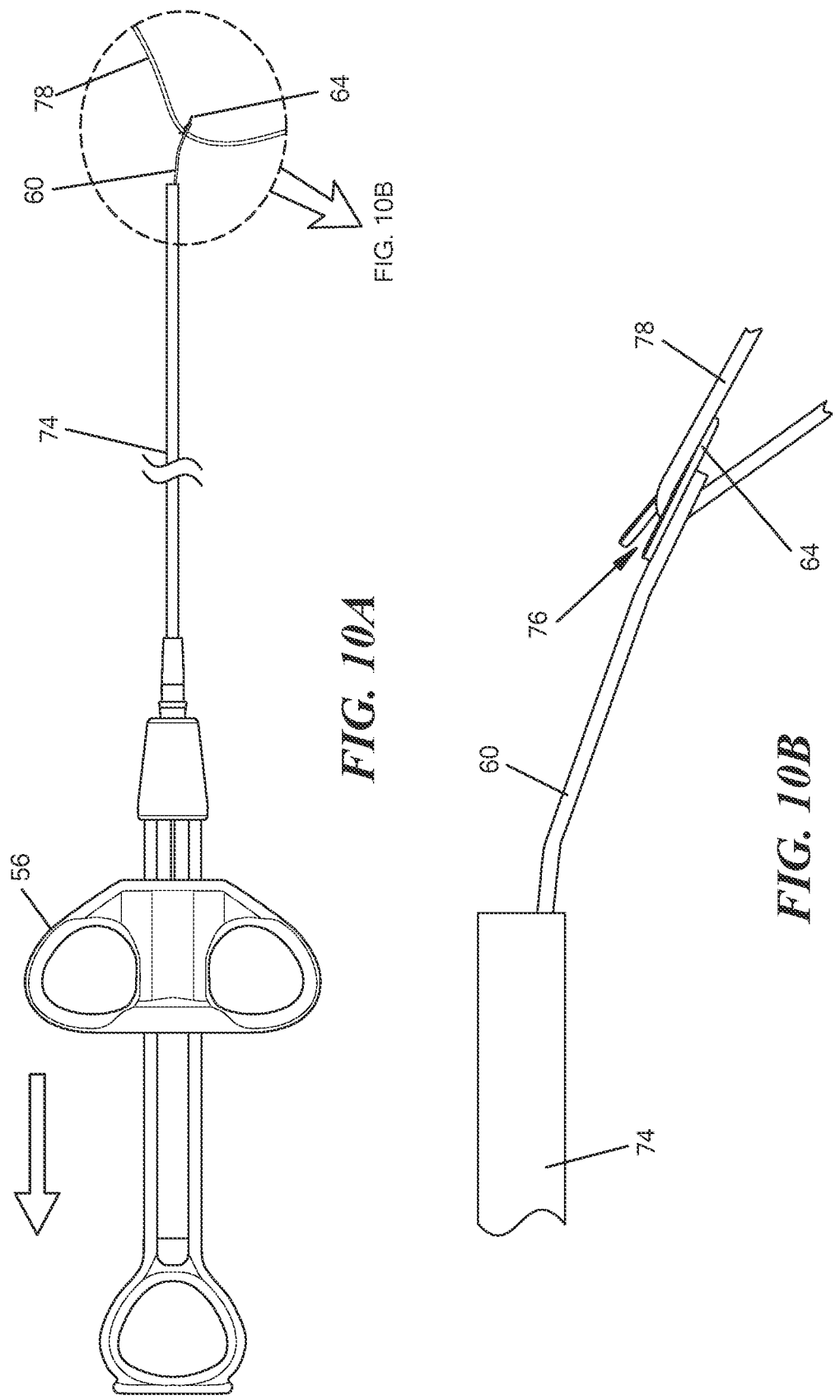

FIGS. 10A-10B schematically show a process of applying tension to the suture in accordance with illustrative embodiments of the invention.

Figure 11A:
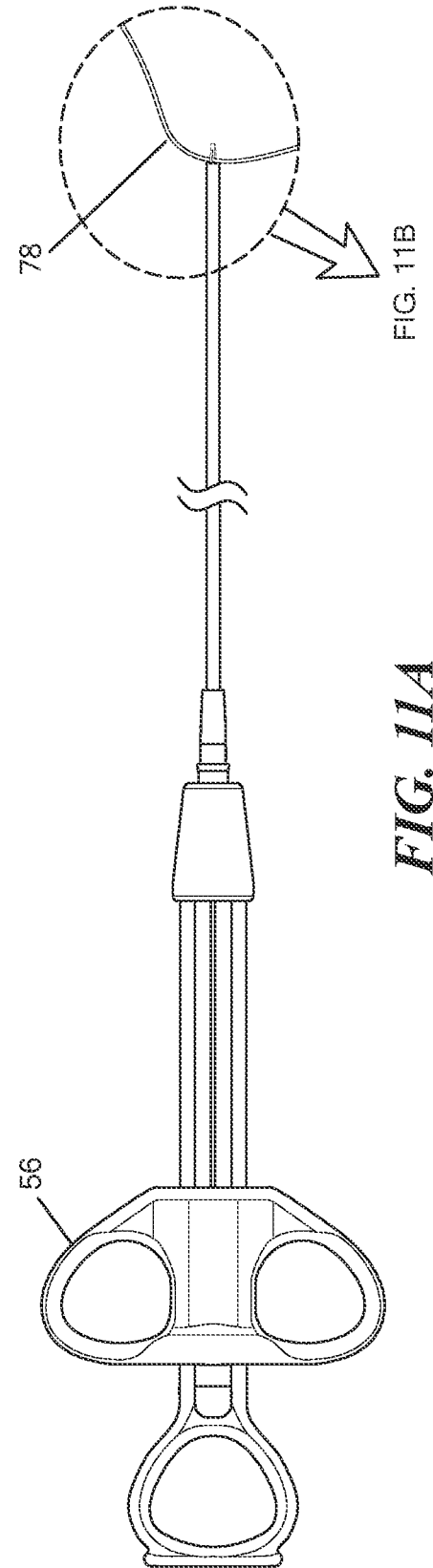
Figure 11B:
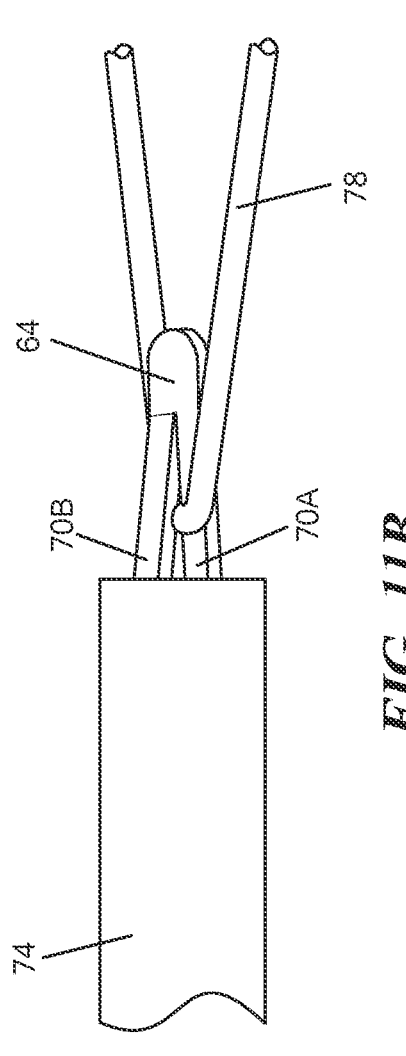

FIGS. 11A-11B schematically show the cutter being further retracted in accordance with illustrative embodiments of the invention.

Figures 12A, 12B:
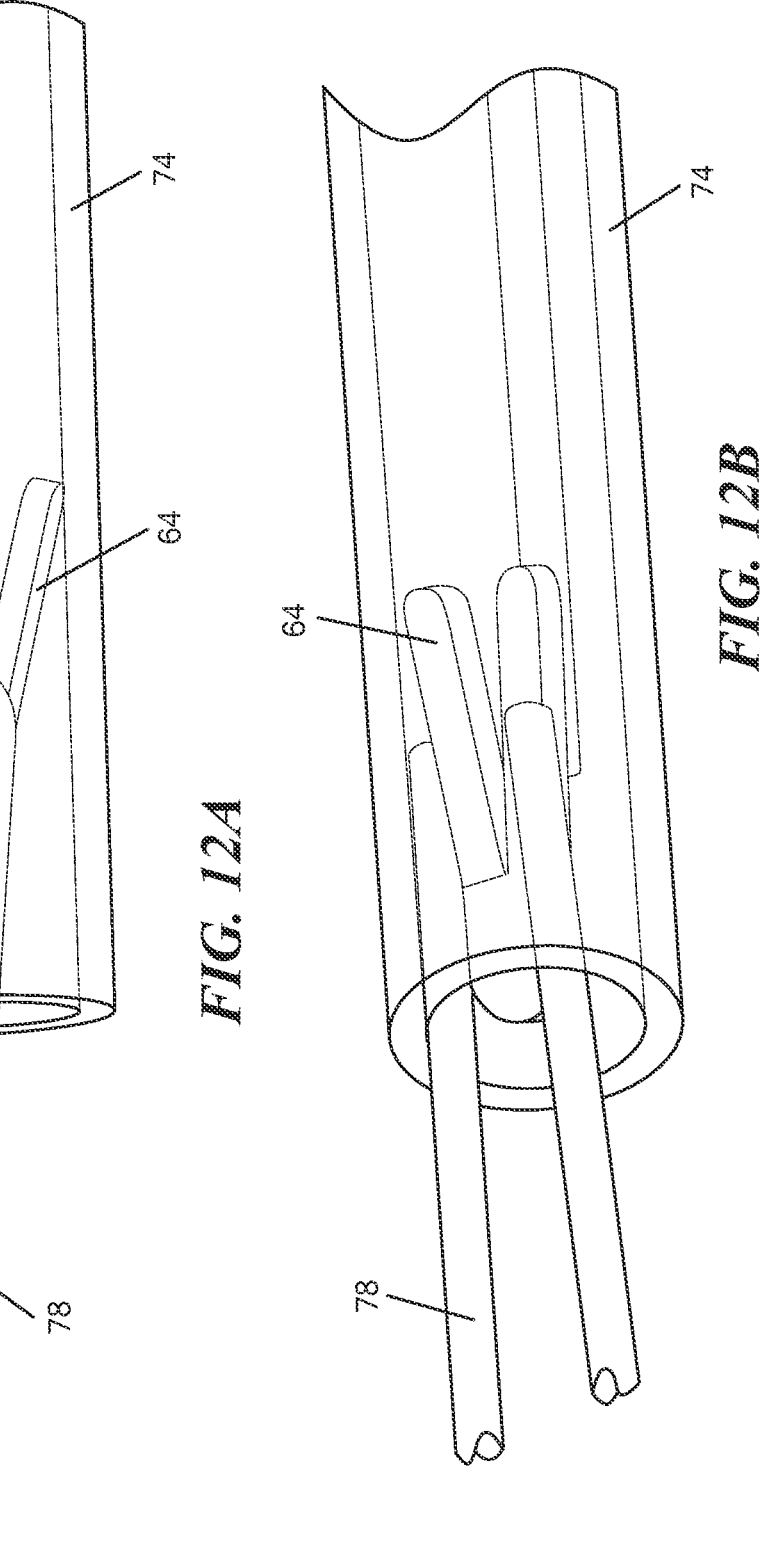

FIGS. 12A-12B schematically show the suture being cut inside the delivery shaft in accordance with illustrative embodiments of the invention.

Figures 13A, 13B:
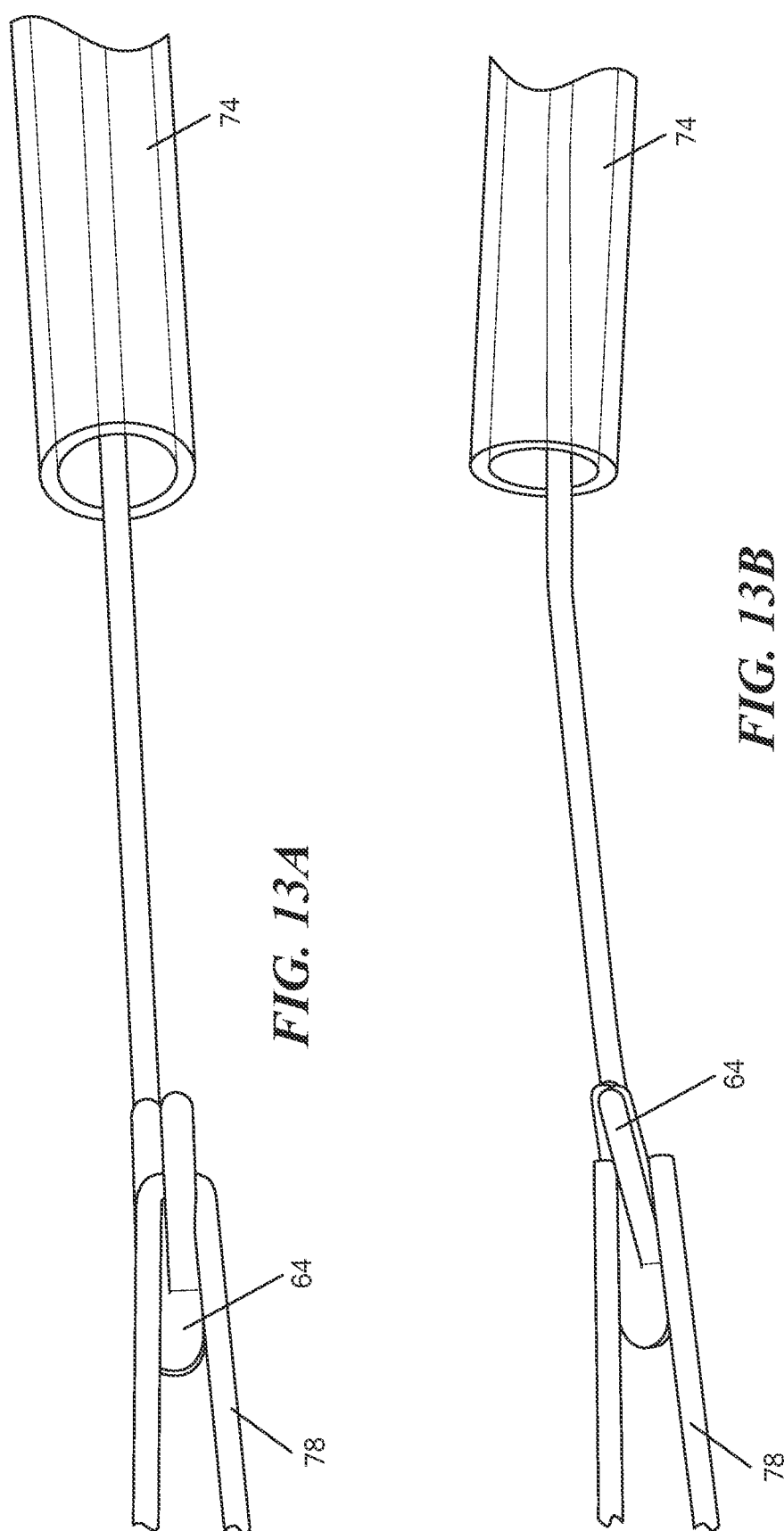

FIGS. 13A-13B schematically show the suture being cut outside the delivery shaft in accordance with illustrative embodiments of the invention.

Figures 14A, 14B, 14C:
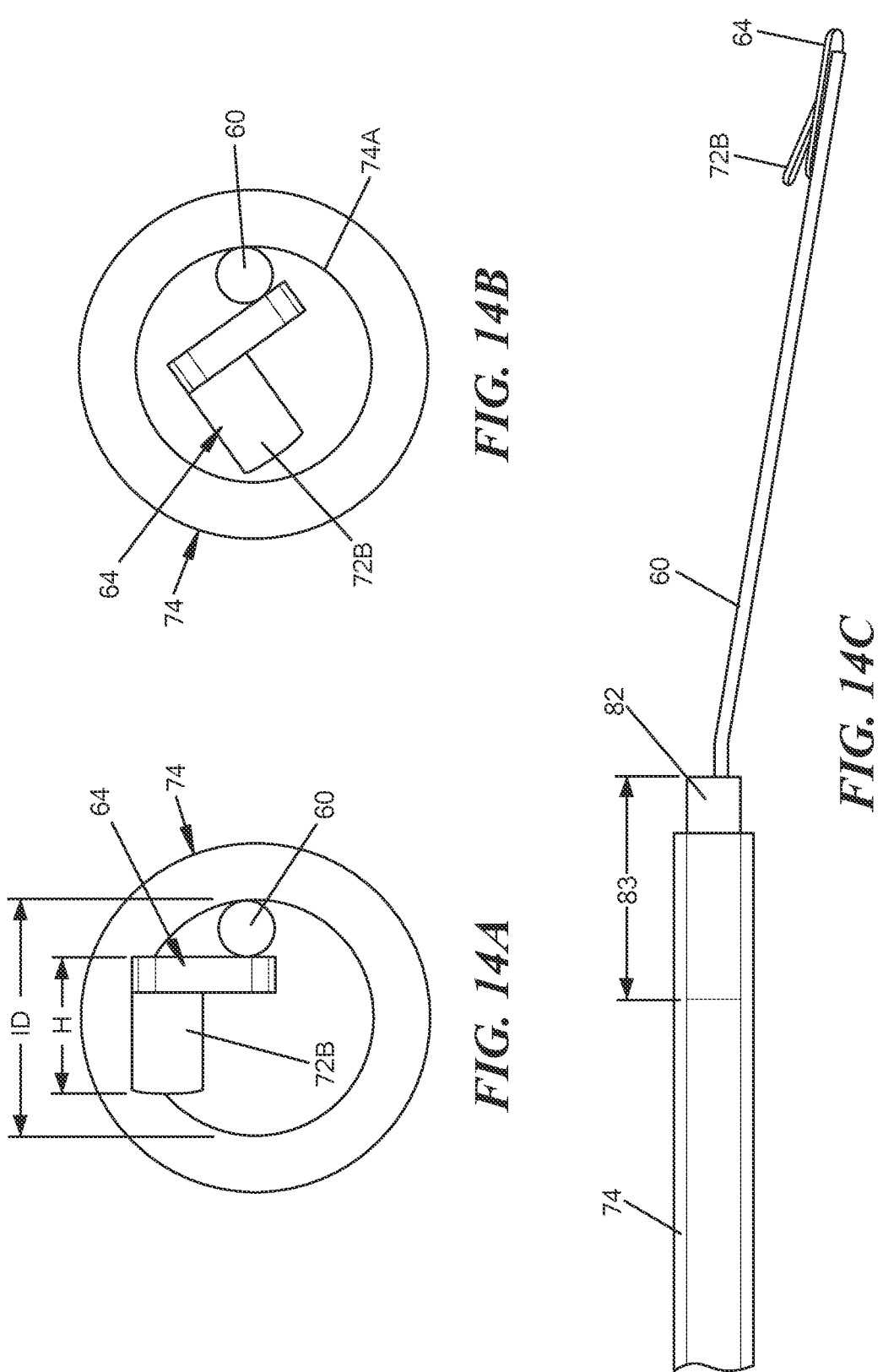
Figures 15A, 15B, 15C:
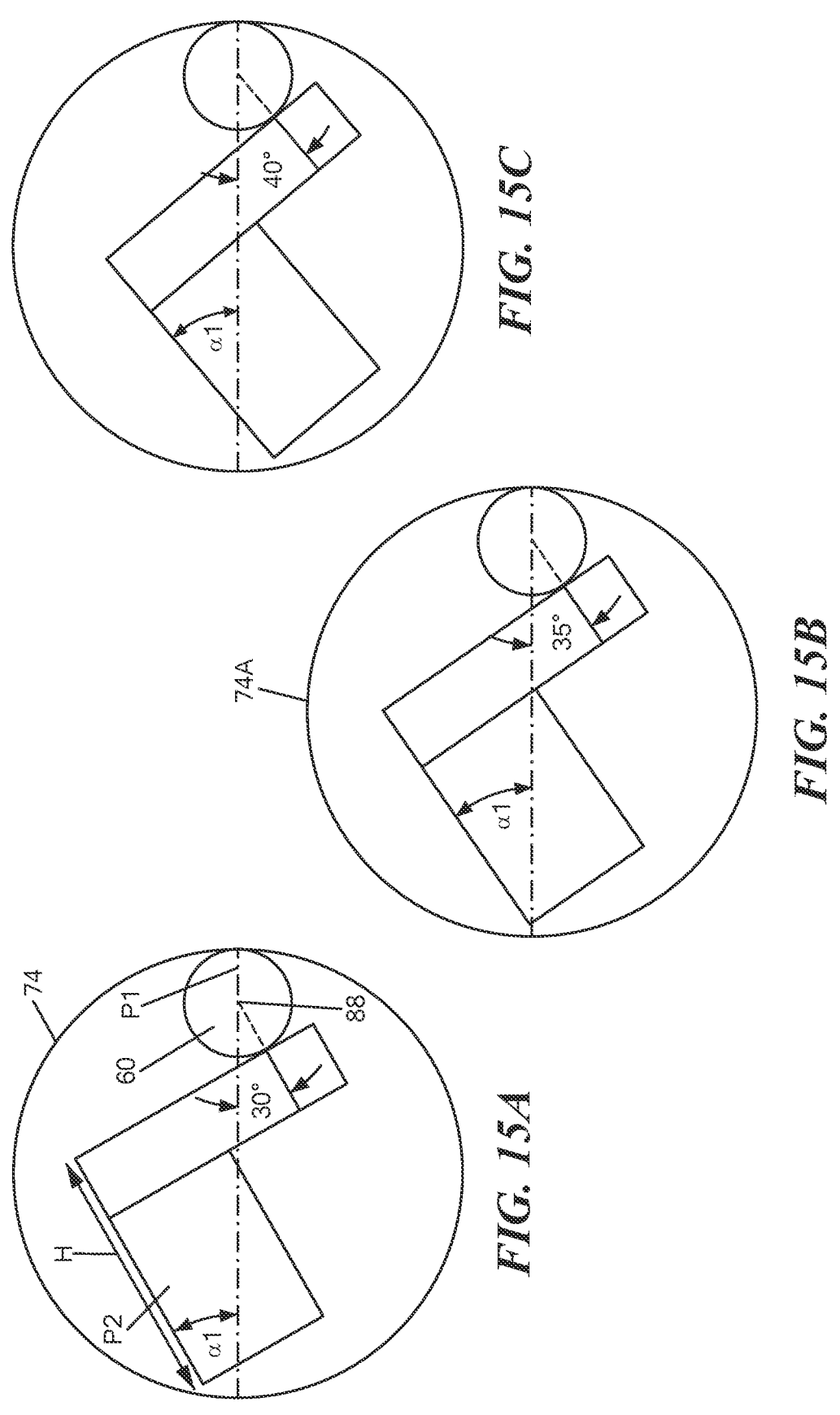
Figures 15D, 15E, 15F:
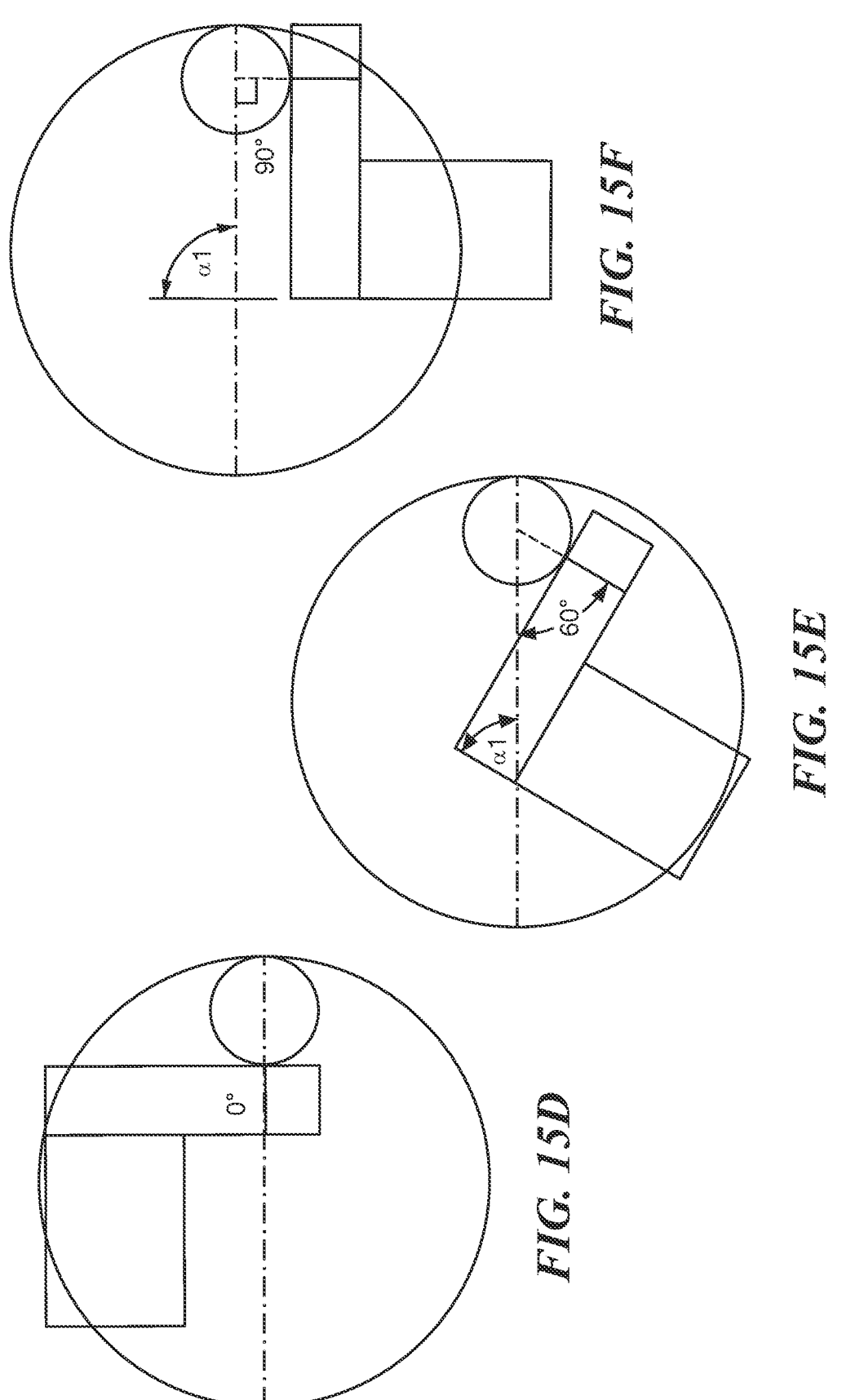
Figure 15G:
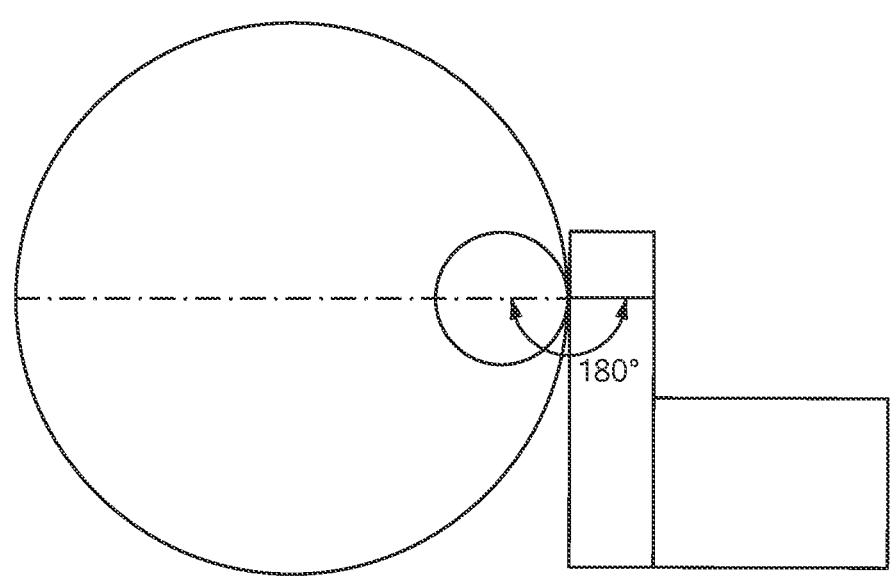

FIG. 14A schematically shows the cutter interfering with the delivery shaft in accordance with illustrative embodiments of the invention.

FIG. 14B schematically shows the cutter not interfering with the delivery shaft in accordance with illustrative embodiments of the invention.

FIG. 14C schematically shows a retraction feature in accordance with illustrative embodiments of the invention.

FIGS. 15A-15G schematically show a variety of cross-sections of various embodiments having the retraction feature in accordance with illustrative embodiments of the invention.

Figures 16, 17:
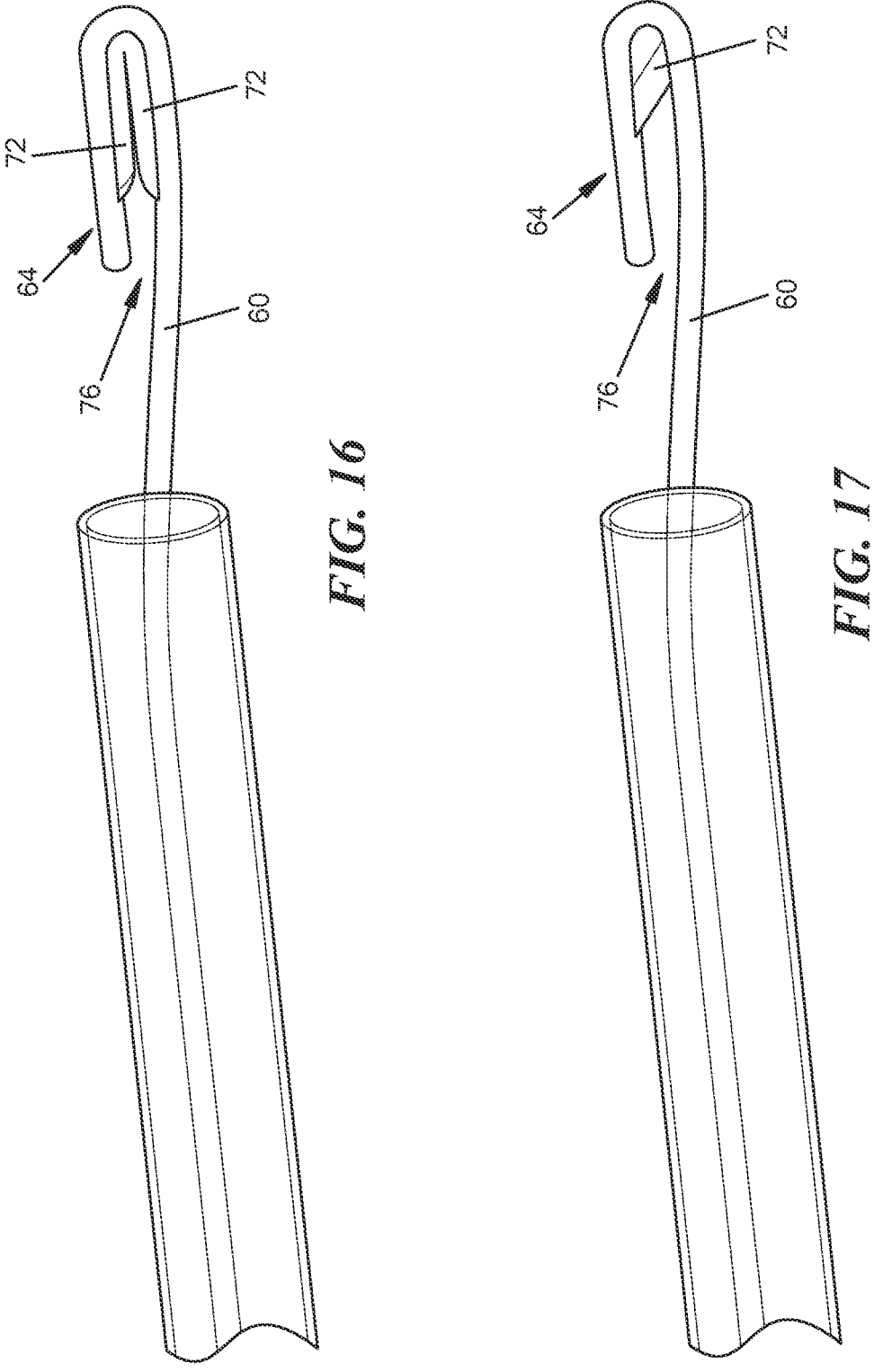
Figure 18:
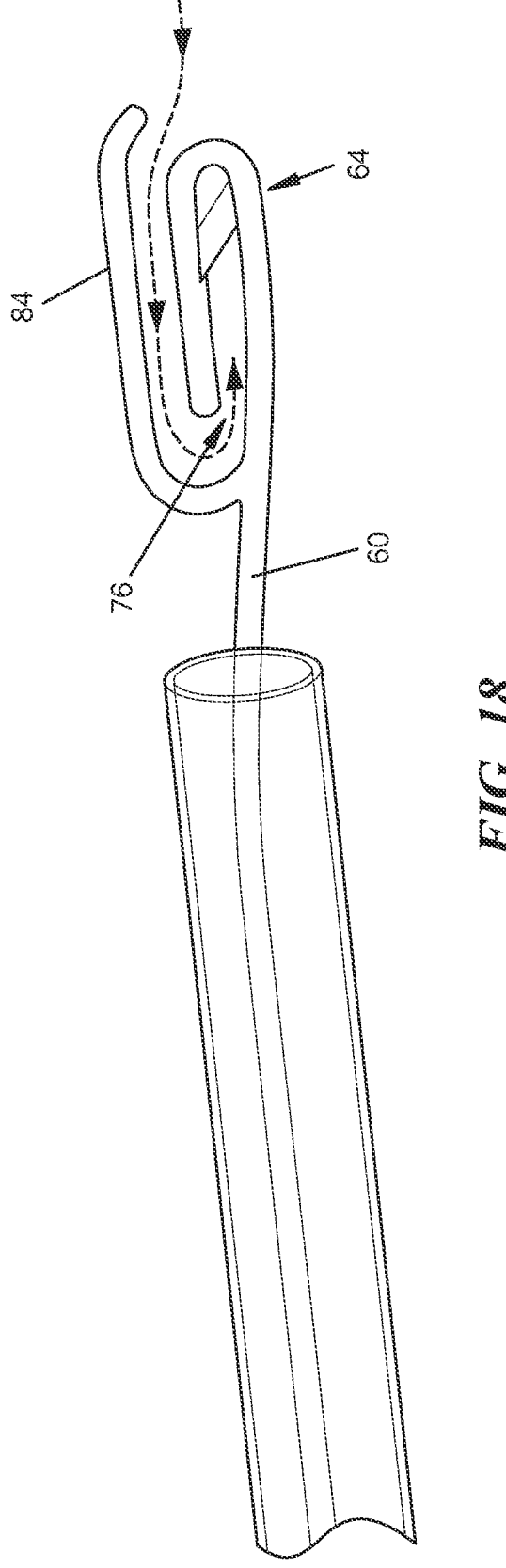

FIGS. 16-18 schematically show alternative embodiments of the suture cutter in accordance with illustrative embodiments of the invention.

It should be noted that the foregoing figures and the elements depicted therein are not necessarily drawn to consistent scale or to any scale. Unless the context otherwise suggests, like elements are indicated by like numerals. The drawings are primarily for illustrative purposes and are not intended to limit the scope of the inventive subject matter described herein.

4

DESCRIPTION OF ILLUSTRATIVE EMBODIMENTS

In illustrative embodiments, an endoscope has a flexible insertion tube with a working channel through which a drive wire coupled with a suture cutter extends. The suture cutter has a relatively small profile and length, such that it navigates through the working channel of the endoscope during a medical procedure. Advantageously, illustrative embodiments are configured to be deployable through the working channel, even when the insertion tube forms a tortuous or winding path. In various embodiments, the suture cutter provides a passive cutting mechanism that does not require active movement and/or independent control of the one or more cutting blades. The cutter has a suture receiving portion that leads to the cutting edge of the blade. The suture receiving portion faces substantially in a proximal direction (also referred to as facing proximally), such that a medical practitioner may capture the suture by pulling the cutter in the proximal direction (pulling the cutter proximally). After the suture is captured, the medical practitioner may cut the suture by applying tension on the suture by further pulling the cutter proximally. Details of illustrative embodiments are discussed below.

In currently available flexible endoscopy suture cutters known to the inventors, the suture is cut using a traditional scissor mechanism with one or two moving blades. Such devices require positioning the blade adjacent to the suture, and manually controlling operation of the blade. Furthermore, cutter tools with a manually movable blade generally have long rigid distal ends (e.g., the cutter tool is about 1 inch long) that make navigating the cutter through the flexible insertion tube difficult, particularly when the insertion tube forms a tortuous or winding path. In contrast, illustrative embodiments capture the suture with the cutter and cut the suture using tension, advantageously reducing the number of moving parts and providing a shorter distal end that better navigates the insertion tube.

Figure 1:
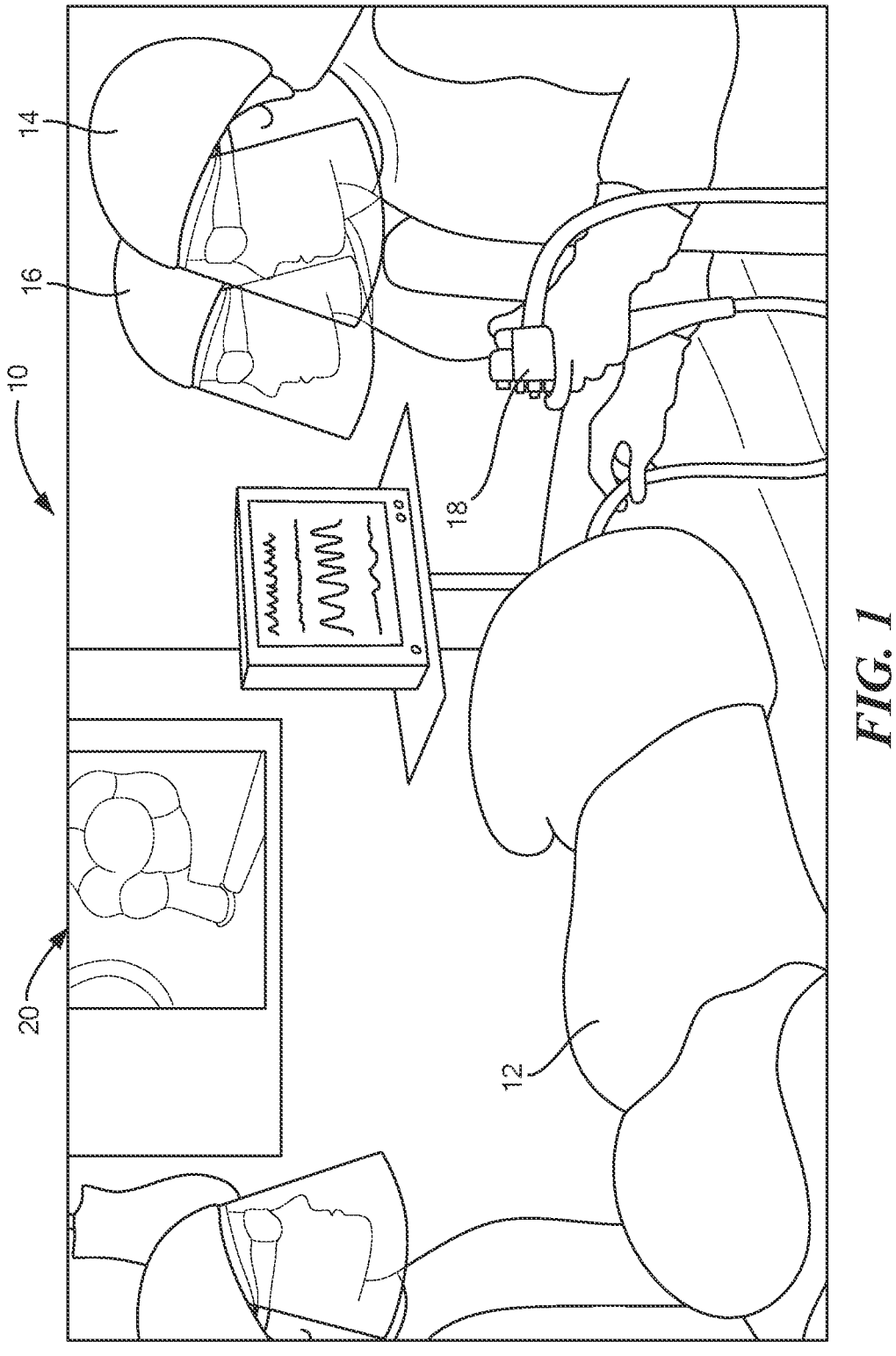
FIG. 1 schematically shows a patient lying on a table in a hospital environment in accordance with illustrative embodiments of the invention.

FIG. 1 schematically shows a patient 12 lying on a surgical table or examination table in a hospital environment 10 in accordance with illustrative embodiments of the invention. The environment 10 may be, for example, within an endoscopy unit of the hospital. The endoscopy unit may include medical practitioners 14 (e.g., gastroenterologists or surgeons), trained nurses 16, and a variety of medical devices. For example, the medical devices may include an endoscope 18, a video display 20, and other equipment. Procedures performed within the endoscopy unit may include gastrointestinal endoscopy (such as gastroscopy, colonoscopy, ERCP, and endoscopic ultrasound), bronchoscopy, cystoscopy, or other more specialized procedures.

FIGS. 2A-2E schematically show the endoscope 18 in accordance with illustrative embodiments of the invention. As known by those in the art, flexible endoscopes 18 (e.g., colonoscope, gastroscope) are positioned into the body of the patient 12 through the body's natural orifices (e.g., mouth, anus). To that end, the endoscope 18 has a long and flexible insertion tube 22 that is adjustable to the natural pathways within the body. Furthermore, the endoscope 18 has a number of channels running through the flexible insertion tube 22. One of these channels is a working channel, through which tools may be advanced to a distal end 23 of the insertion tube 22.

The endoscope 18 may be contrasted with other devices such as laparoscopes, which are not inserted into the patient's 12 natural orifices. Instead, laparoscopes are inserted into one of the access holes made in the patient 12 during a laparoscopic procedure. Usually, three access holes are made for laparoscopy procedures, one for the rigid scope, and two ports for the tools such as forceps, scissor, suture, etc. Laparoscopes have a non-flexible, rigid, and short insertion tube that is sent through one of the access holes into the body. Generally, laparoscopes do not have a working channel for running tools therethrough. In contrast, the insertion tube 22 of the endoscope 18 (colonoscope, gastroscope) is flexible to travel through the body's natural orifices and has a working channel. Various embodiments may be used with a variety of scopes, such as laparoscopes. However, preferred embodiments are used with a flexible insertion tube 22.

The endoscope 18 has a control section 26 to help guide the insertion tube 22 through the patient's 12 bodily pathways (e.g., the winding GI tract). To that end, the endoscope 18 includes control dials 26 that allow control of the position and orientation of the insertion tube 22 (e.g., bending of the distal end 23 up or down, and right or left). Like many endoscopes, the endoscope 18 may have a plurality of imaging controls, such as an image freeze button and image capture button. There may also be control chromoendoscopy buttons that may change the color of the video in the display 20. The control section 26 may also include a suction button 28 and an air/water button 30. The endoscope 18 may be connected to a light supply via a light guide 31, an air supply via an air supply connector 32, a water supply via a water supply connector 34, and a suction supply via a suction connector 36. Thus, light, air, water, and/or suction, may be delivered through the umbilical cord 35 to the distal end 23 of the insertion tube 22 through the various aforementioned channels.

Water, air, suction, and other functions may selectively be applied at the distal end 23 via separate channels within the insertion tube 22. For example, the user may press the water button 30 to selectively spray water out of the distal end 23. To that end, water is pulled from an external water supply through the water supply connector 34, passes through an umbilical cord 35 of the endoscope 18, and then goes down the insertion tube 22 and out of the distal end 23. A similar process is followed for other functions, including light and suction. Each of these functions may have a dedicated channel within the endoscope 18.

FIG. 2B schematically shows a partially exposed view of the insertion tube 22 in accordance with illustrative embodiments. The insertion tube 22 has a plurality of channels 38-41 and wires 42-45 within the insertion tube 22 that are configured to provide various utility to the endoscope 18. For example, the insertion tube 22 includes the biopsy channel 38, an air channel 39, a water channel 40, and a water jet channel 41. The insertion tube 22 may also include light guide fibers 42, a wire for adjustable stiffness 43, angulation wires 44, and CCD signal wires 45, among other things. These channels 38-41 and wires 42-45 are within a housing of the insertion tube 22. The housing of the insertion tube 22 may include an out outer polymer top coat 46 and base layer. Underneath the polymer top coat 46 may be a stainless steel wire mesh 47, along with an outer spiral metal band 48 an inner spiral metal bands 49.

FIG. 2C schematically shows the distal end 23 of the insertion tube 22 with a tool 50 extending out of the working channel 38 in accordance with illustrative embodiments of the invention. The tool 50 may be positioned in the working channel 38 by passing through an accessory port 37 (shown in FIG. 2A). For example, FIG. 2C schematically shows a biopsy forceps 50 extending out of the working channel 38. Various embodiments use a cutting device 54 to deliver a suture cutter 64 via the working channel 38. The cutting device 54 may also be referred to as a cutter delivery device 54.

FIG. 2D schematically shows the endoscope of FIG. 2A with the endoscope substantially straight near the distal end 23 of the insertion tube 22. FIG. 2E schematically shows the endoscope of FIG. 2A with the position and orientation of the insertion tube 22 adjusted (e.g., angulated). In particular, the control section 26 is used to bend the distal end 23. In practice, the medical practitioner 14 controls the bending of the insertion tube 22 to orient the distal end 23 appropriately within the patient 12 during a procedure. For example, the insertion tube 22 may be bent in various ways for traversing the GI tract. When the distal end 23 is near the desired location, the distal end 23 orientation is manipulated (e.g., to take a particular biopsy sample, to capture a particular suture, etc.). When the distal end 23 is oriented appropriately, the tool 50 may be extended out of the working channel 38. However, when the distal end 23 of the tool 50 (e.g., cutter, biopsy forceps, scissor, etc.) is rigid, it is difficult to advance the tool 50, particularly when the endoscope 18 distal end is angulated as shown in FIGS. 2E and 2F.

FIG. 2F schematically shows the endoscope of FIG. 2A with a curved portion 21 of the insertion tube 22 near the distal end 23. In some use cases, the insertion tube 22 may be curved considerably, particularly near the distal end 23, to achieve the desired orientation relative to the patient 12 and/or suture 68. When the desired orientation is achieved, one or more tools 50A and 50B may be advanced out of the one or more working channels 38. For example, as shown in FIG. 2F, the tools 50 may be, among other things, an endoscopic scissor 50B and an endoscopic snare 50A. However, various embodiments may advance other tools 50, such as a biopsy forceps and/or an endoscopic clip out of the working channel 38. Each of the tools 50 may be said to have a rigid longitudinal traversal length L as the tool 50 is advanced through the insertion tube 22 and/or out of the working channel 38. However, as discussed below, some tools 50 may have a negligible rigid length.

For example, the endoscopic scissor 50B has a rigid longitudinal traversal length L as it traverses the insertion tube 22 and is advanced out of the working channel 38. The rigid longitudinal traversal length L of the scissor 50B is defined by the rigid length of the tool 50 as it travels through the insertion tube 22. For example, the scissor 50B traversal length L is determined when the blades are closed (because the scissor 50B travel through the insertion tube 22 with the blades closed).

As another example, a snare tool 50A is another tool 50 that may be used with various embodiments. The snare tool 50A includes a flexible snare portion 68 that extends out of a flexible delivery housing 69. The snare portion 68 is flexible during the normal operation of the endoscope 18, and thus, includes a negligible rigid component. The snare portion 68 extends out of the flexible delivery device 69 after the delivery device 69 is extended out of the working channel 38. Because the delivery device 69 is flexible, it too has a negligible rigid length as it traverses through the insertion tube 22. In other words, the delivery device 69, and the snare portion 68 flex to accommodate to the shape of the insertion tube 22 as they travel inside of the insertion tube 22. Accordingly, during normal use, the medical practitioner 14 does not have to adjust the shape of the insertion tube 22 to allow passage of the snare tool 50A.

As yet another example of a tool 50, some embodiments may include a suture cinch tool 50, which is described, example, in U.S. patent application Ser. No. 17/991,526, which is incorporated herein by reference.

One skilled in the art should appreciate that longer rigid lengths L make it more difficult for the tool 50 to navigate the flexible insertion tube 22 and/or to exit the distal end 23. Depending on the curvature/angulation of the insertion tube 22, some longer rigid lengths L may be impossible to navigate through the insertion tube 22 (e.g., out of the distal end 23). Therefore, various embodiments advantageously provide a tool 50 with a small rigid length L. For example, the endoscopic suture cutter 64 rigid length L is small (about 0.1 inch to about 0.3 inch), allowing for easier device advancement and better access when the endoscope distal end 23 is not in the straight orientation. This is in contrast to the rigid length L of endoscopic scissors, (0.5 inch to about 1.0 inch). When the distal end 23 of the endoscope 18 is angulated, it is difficult and sometimes impossible to advance the scissor inside the working channel 38 at angulated regions. Instead, the practitioner 14 needs to straighten the tip of the endoscope 18 to advance the scissor inside the working channel. Illustrative embodiments allow the practitioner 14 to advance the cutter 64 inside the working channel 38 at angulated regions.

FIG. 3A schematically shows a cutting device 54 in accordance with illustrative embodiments. The cutting device 54 includes a cutter deployment system 62 configured to be positioned within the insertion tube 22 and to move a cutter 64 through the insertion tube 22. As described below, the cutter deployment system 62 includes a delivery shaft 74, a drive wire 60 within the delivery shaft 74, and the cutter 64 coupled to the drive wire 60, among other things. The cutter deployment system 62 is controlled externally of the insertion tube 22. To that end, the cutting device 54 includes a handle slider 56 with openings configured to receive the practitioner's 14 thumb fingers. During use, the handle slider 56 slides along a handle frame 58. Movement of the handle slider 56 relative to the handle frame 58 causes the drive wire 60 inside the delivery shaft 74 to move proximally or distally along the delivery shaft 74. As shown in FIG. 9, the handle frame 58 and handle slider 56 may be rotated to rotate the cutter 64.

In various embodiments, the drive wire 60 (also referred to as a pull wire 60) may be movable in an axial direction (e.g., substantially along A1) within the delivery shaft 74. Axis A1 is a central longitudinal axis that runs through the working channel 38. The drive wire 60 may be a long pull wire 60, supported inside the delivery shaft 74. In some embodiments, the drive wire 60 may comprise a long pull wire 60 such as a solid wire, strander wire, or a combination of both. In some embodiments, the drive wire 60 may comprise a long pull wire 60 inside a spring guide 65 and/or the delivery shaft 74 for support. The spring guide 65 may be internal to the delivery shaft 74 and supports the pull wire 60. In some embodiments, the delivery shaft 74 may comprise a long catheter without any spring guide 65. The pull wire 60 has a small diameter and may not have a structural support on its own. In various embodiments, the delivery shaft 74 or/and spring guide 65 provides the structural support to the pull wire 60 (while going through working channel, etc.) while going through working channel 38, etc.).

In various embodiments, the pull wire 60 is inside the delivery shaft 74 (e.g., a catheter). Some embodiments therefore may not include the Bowden coil 65. Some embodiments may use a coil instead of a catheter, or both the coil and a jacket. As mentioned previously, the pull wire 60 has a small diameter and generally does not have a structural support on its own. Therefore, in various embodiments, the pull wire 60 can be supported by a delivery catheter, a delivery coil, and/or a delivery coil with jacket (catheter).

It should be understood that although axis A1 is shown as a straight axis, that in various embodiments, the delivery shaft 74 is configured to bend and/or twist in a manner similar to the insertion tube 22, and thus the axis A1 may also be curved, bent, and/or twisted. Therefore, in various embodiments, moving the drive wire 60 and/or the cutter 64 along the axis A1 may not be straight line axial movement. Furthermore, in some embodiments, the distal end of the drive wire 60 may be bent, such that the drive wire 60 forms a central cutter axis B1 that diverges from the central axis A1 of the insertion tube 22. When the cutter axis B1 diverges from central axis A1, the pull wire 60 can be forced against the internal diameter of the delivery shaft 74. This provides maximum space for the cutter 64 to move proximally and distally in the delivery shaft 74. Additionally, the diverging cutter axis B1 allows the rotation of cutter 64 into an arc when extended distally. This enables a larger area of reach for the cutter 64 to capture suture 78.

FIGS. 3B-3F schematically show detailed views of the cutter 64 in accordance with illustrative embodiments of the invention. The cutter 64 is configured to cut one or more sutures that have been sutured within the patient 12 (e.g., within the GI tract). To that end, the cutter 64 has a suture receiving portion 76 configured to guide or lead the suture to one or more sharp edges 70. In FIG. 3B, the cutter 64 has four sharp edges 70. Two of the sharp edges 70 are used to cut the suture. The sharp edges 70 may each be part of a cutting blade 72A and 72B. In some embodiments, the first cutting blade 72A may be planar with the main body 80 of the cutter 64. For example, the cutting blade 72A may be formed from the main body 80. The second cutting blade 72B may be out-of-plane with the first cutting blade 72A and/or the main body 80 (e.g., biased upwardly) such that the suture receiving portion 76 is formed by the blades 72A and 72B. In some embodiments, the first blade 72A defines a first plane, and the second blade 72B defines a second plane that is non-parallel to the first plane. In some embodiments, the first blade 72A, the second blade 72B, and the main body 80 may all have substantially non-parallel planes (as shown in FIGS. 3E and 3F).

When the suture 78 is positioned in the suture receiving portion 76, the cutter 64 may be pulled in a proximal direction to effectuate the cutting of the suture 78. Specifically, the suture 78 may be cut by applying tension on the suture 78 with the blades 72A and 72B (e.g., by a user pulling the handle 56 to move the wire 60 coupled with the cutter 64 in a proximal direction). The sharp blades 72A and 72B are forced against the suture 78 and cut the suture 78.

It should be apparent that although various embodiments show and describe two blades 72A and 72B, this is not intended to limit various embodiments of the invention. Some embodiments may have only a single blade 72 with the sharp edge 70. For example, some embodiments may have only the planar blade 72A. Some other embodiments may have only the out-of-plane blade 72B. Embodiments with a single blade 72 may still form a suture receiving portion 76 (e.g., using a second dull edge instead of the second sharp edge 70). For example, some embodiments may include one or more arc-shaped or semi-circular blade 72. Thus, discussion to a singular blade 72 or multiple blades 72 is not intended to limit various embodiments of the invention. For example, the suture receiving portion 76 may be formed by one or both of the blades 72A and 72B.

The cutter 64 advantageously operates as a passive tension cutter, i.e., no user control or active movement of the blades 72A in 72B is needed to cut the suture 78. Instead, tensioning the suture 78 against the sharp edge 70 cuts the suture 78. In various embodiments, the out-of-plane blade 72B may be biased upwardly (e.g., resilient) or rigidly formed.

In various embodiments, the cutter 64 may be formed (e.g., stamped, electrical discharge machined) from a thin sheet of material (e.g., metal or plastic). In some embodiments, the thickness T of the material of the cutter 64 is 1 mm or less (e.g., T1 and T2 are each less than 1 mm). Furthermore, the out-of-plane blade 72B may cause the cutter 64 to have a greater overall height H than the thickness T. In various embodiments, the height H of the cutter is between about 1.3 mm and 3.5 mm. The overall width W of the cutter 64 may be between about 1 mm and about 2 mm. The overall rigid length L of the cutter 64 may be between about 4 mm and about 8 mm. Preferably, the external edges 75 (e.g., distal edges or proximal edges) of the cutter 64 are dull or rounded to prevent accidental cutting of the patient 12. The opening O of the suture receiving portion 76 (e.g., formed by the two blades 72) allows the cutter 64 to grab and receive the suture 78. If the opening O is too small, it is difficult to capture or properly place the suture 78 between the two blades 72. If the opening O is too large, it becomes difficult to retract the blade 72 into the delivery shaft 74 (e.g., see FIG. 14A). Preferably, the opening O is between 0.9 mm and 3.1 mm. For clarity, ranges between endpoints X and Y and considered to include the end-points X and Y.

In various embodiments, the non-moving cutting edges 70A and 70B meet at a cutting point 71 that provides effective cutting of the suture 78 as opposed to a regular scissor style cutter where two opposing blades move against each other to create a moving cutting point. In various embodiments, the two blades 72A and 72B do not move to cut. Preferably, the blades 72 are rigid and short enough that they do not move when used regularly to cut the suture 78. The blades 72A and 72B may therefore be considered static blades 72A and 72B. Although the static blades 72A and may be formed from material that can be deformable or malleable under application of sufficient force (i.e., under non-normal use), the blades 72A and 72B are still considered to be static/non-moving during normal use by the medical practitioner 14 (e.g., when applying force sufficient to cut the suture 78).

In various embodiments, depending on the thickness of the suture 78, the suture 78 may be cut at a cutting region 73 formed between the cutting edges 70A and 70B of the two blades 72. In some embodiments, the suture 78 may reach the cutting point 71. However, in some other embodiments, the suture 78 may be cut within the cutting region 73 formed by the blades 72.

FIG. 4 shows a process 400 of cutting a suture 78 in accordance with illustrative embodiments of the invention. It should be noted that this process is simplified from a longer process that normally would be used to cut the suture 78. Accordingly, the process 400 of cutting the suture 78 likely has many steps that those skilled in the art likely would use. In addition, some of the steps may be performed in a different order than that shown. Additionally, or alternatively, some of the steps may be performed at the same time. Those skilled in the art therefore can modify the process 400 as appropriate.

The process 400 begins at step 402, where the medical practitioner 14 sutures a perforation inside of the patient 12.

For example, during the medical procedure, the medical practitioner 14 may take a biopsy from the patient 12 by using the biopsy tool 50 (e.g., biopsy forceps) to remove a polyp. The biopsy tool 50 may be placed within the working channel 38 of the endoscope 18. The medical practitioner 14 may then use any suturing tool 50 to suture the perforation. In various embodiments, the suturing tool may be attached to the outside of the distal end 23 of the insertion tube 22. Various embodiments of the endoscope 18 may include one or more working channels 38.

The process of suturing a perforation is known in the art and therefore is not described in great detail here. In general, the process involves grasping tissue near the perforation (e.g., using a tissue grasping tool 50), retracting the tissue, driving a needle coupled to the suture 78 through the tissue, and repeating the stitches as desired. Thus, in the above-described example, the suture 78 has two ends: a first end coupled with the needle, and a second free end. Various embodiments may cinch the free end of the suture and/or the first end coupled with the needle together or separately. In some other embodiments, the suture is coupled to a needle that is part of a needle assembly (e.g., that passes through the tissue and grips the tissue). The suture may thus be considered to have a single free end, and a second anchored end. The suture may be formed of any materials commonly used for surgical suture, such as stainless steel, nitinol, nylon, braided polyester, polypropylene, and/or silk. Some may also be used to cut sutures 78 having two free ends.

The process proceeds to step 404, which provides the endoscopic suture cutting device 54, such as the device 54 shown in FIGS. 3A-3B. The device 54 may be provided to the medical practitioner 14 during and/or after a medical procedure, such as a polypectomy. Illustrative embodiments work with a variety of sutures and/or endoscopic suturing devices. Advantageously, the suture cutting device 54 may be used to cut the suture that was previously applied to the patient 12 (e.g., to a perforation) using an integrated or separate stitching tool.

The process proceeds to step 406, which positions the cutter deployment system 62 into the working channel 38 of the endoscope 18. To remove a suture 78 in the gastrointestinal tract, the patient 12 may be intubated with the endoscope 18. After positioning the endoscope 18 inside of the patient 12 and locating the suture 78 to be cut, the practitioner 14 inserts the deployment system 62 into the accessory port 37 of the endoscope 18. Alternatively, the deployment system 62 may be positioned in the accessory port 37 before positioning the endoscope 18.

Specifically, a distal end of the delivery shaft 74 may first be positioned within the accessory port 37 of the endoscope 18. FIG. 5 schematically shows the cutter deployment system 62 positioned in the accessory port 37. In particular, the delivery shaft 74 is driven into the accessory port 37. The delivery shaft 74 may advantageously flex in a manner corresponding to the shape of the insertion tube 22.

At step 408, the suture cutter 64 is extended from the working channel 38 of the endoscope 18. FIGS. 6A-6B schematically show the suture cutter 64 transitioning from being inside the delivery shaft 74 to extending outside of the delivery shaft 74 in accordance with illustrative embodiments of the invention.

In particular, FIG. 6A shows the cutter 64 inside the delivery shaft 74. From the practitioner 14 perspective, the handle 56 is in a retracted position. To extend the suture cutter 64 from the working channel 38, the handle 56 is moved forward after the delivery shaft 74 is outside of the working channel 38 of the endoscope 18, as shown in FIG. 6B.

FIG. 7 shows a perspective view of the suture cutter 64 extended from the working channel 38 of the endoscope 18 in accordance with illustrative embodiments of the invention. In contrast to many prior art cutting tools, in various embodiments of the cutter 64, the suture receiving portion 76 defines an opening or a gap that substantially faces in a proximal direction (i.e., faces towards the working channel 38 and/or the distal end 23 of the endoscope 18).

In some embodiments, the pull wire 60 may be configured to extend the cutter 64 straight out of the delivery shaft 74. However, in some other embodiments, and as shown in FIG. 7, the pull wire 60 may be configured to bend as it exits the delivery shaft 75. Accordingly, a central axis B1 of the cutter 64 may form an axis B1 that diverges from the central axis A1 by an angle Θ1. In various embodiments, the angle Θ1 may be between about 5 degrees and about 30 degrees, or between about 10 degrees and about 20 degrees.

Advantageously, a proximal facing suture receiving portion 76 allows the practitioner 14 to hook the suture 78 with the suture receiving portion 76, and to cut the suture 78 with a simple retraction of the cutter 64 (e.g., pulling the drive wire 60 in a proximal direction). Additionally, the cutter 64 does not require independent and active control of the blades 72A and 72B. Instead, as described below, the suture 78 is positioned into the suture receiving portion 76 and then cut by the blade 72 using the tension on the suture 78. Because there is no movement of the blades 72A and 72B against each other, no pivoting mechanism is required. However, some embodiments may still have some biasing/movement of the passive blades 72. Illustrative embodiments thus provide a passive/static cutting mechanism using a passive planar blade 72A and/or out-of-plane (e.g., biased) blade 72B. Accordingly, the cutter 64 is advantageously considerably shorter and thinner than many prior art cutters and easily navigates through the insertion tube 22.

After the suture cutter 64 is extended, the suture 78 is positioned in the suture receiving portion at step 410. FIGS. 8A-8C schematically show the suture 78 being positioned in the suture receiving portion 76 in accordance with illustrative embodiments of the invention. As shown in FIGS. 8A-8B, the cutter 64 is advanced forward until it is distal to the suture 78. A portion of the opening of the suture receiving portion 76 is aligned with at least a portion of the suture 78 (as represented by the dashed line in FIG. 8B). The handle 56 may be manipulated until the suture 78 comes to be positioned (e.g., hooked) into the suture receiving portion 76. FIG. 8C schematically shows a close-up view of the suture 78 positioned in the suture receiving portion 76 in accordance with illustrative embodiments of the invention. At this point, the suture 78 can be said to be "captured" or "hooked" by the cutter 64.

In various embodiments, the cutter 64 may need to be rotated to properly align the opening of the receiving portion 76 with the suture 78. FIG. 9 schematically shows a rotation feature of the cutting device 54 in accordance with illustrative embodiments of the invention. As described previously, the cutting device 54 may be coupled with the endoscope 18. In illustrative embodiments, the handle 56 may be rotated to rotate the cutter 64. Accordingly, the receiving portion 76 is advantageously rotatable to allow easy alignment and capture of the suture 78. For example, the rotation allows repositioning the receiving portion 76 to an ideal location to capture the suture 78. To that end, in various embodiments, the pull wire 60 is coupled to the handle slider 56, and the delivery shaft 74 is coupled to the coupler 61 (shown in FIG. 3A). This allows relative rotation of the drive wire 60, and thus the cutter 64, relative to the flexible tubing 22 and the delivery shaft 74.

In various embodiments, the handle 56 is outside of the accessory port 37 and is manipulated by the medical practitioner 14. To go through the working channel 38, the delivery shaft 74 is preferably long for endoscopic procedures (e.g., about 150 cm to about 250 cm).

The process then proceeds to step 412 which applies tension to cut the suture 78 with the suture cutter 64. FIGS. 10A-10B schematically show the process of applying tension to the suture 78 in accordance with illustrative embodiments of the invention. FIG. 10B shows a detailed view of FIG. 10A. In various embodiments, tension may be applied by retracting the suture cutter 64. To that end, the handle 56 is pulled proximally (as represented by the arrow). FIGS. 10A-10B schematically show the suture cutter 64 retracting with the captured suture 78 in accordance with illustrative embodiments. As the suture cutter 64 retracts, the suture 78 is tensioned. Upon application of sufficient tension, the suture 78 is cut by the blades 72A or 72B. Depending on the type of suture 78, additional tension may be necessary. The captured suture 78 may be further tensioned by pulling the suture cutter 64 and/or the entire cutter deployment system 62 further proximally. FIGS. 11A-11B schematically show the cutter 64 being further retracted in accordance with illustrative embodiments.

Various embodiments advantageously cut the suture 78 by pulling substantially in a proximal direction. Because the practitioner 14 pulls in the proximal direction (away from tissue) to cut the suture 78, illustrative embodiments advantageously provide additional safety compared to traditional endoscopic scissors. With endoscopic scissors, the practitioner 14 cuts the suture towards the tissue (distally) which may undesirably cut the tissue (e.g., accidentally if the blade tip is close to tissue). In illustrative embodiments, the practitioner 14 cuts the suture 78 by pulling away from tissue (i.e., by pulling the cutter towards a proximal direction), which reduces the likelihood of cutting and injuring the tissue.

Based on testing, the inventors have determined that the suture 78 is cut either outside or inside of the delivery shaft 74 when the right amount of tension is applied. Based on the type of the suture 78 (e.g., a smaller size suture is cut easier than a larger size suture) and the amount of the suture under tension during procedure, the suture 78 may be cut before it is pulled into the delivery shaft 74 or the handle might need to retract the blade 72 and the suture 78 further into the delivery shaft 74 to apply higher tension on the suture to cut it. The more the cutter 64 is retracted into the delivery shaft 74, the more tension is applied on the suture 78.

However, in some embodiments, the cutter 64 may face in a substantially distal direction, such that the suture receiving portion 68 faces substantially distally. Accordingly, some embodiments may simply push the cutter 64 towards the suture 78 to cut the suture 78 (e.g., by pressing the handle distally). Of course, some other embodiments may position the cutter 64 in a proximally-facing direction, such that the cutter 64 may be pulled to cut the suture 78.

FIGS. 12A-12B schematically show the suture 78 being cut inside the delivery shaft 74 in accordance with illustrative embodiments of the invention. FIGS. 13A-13B schematically show the suture 78 being cut outside the delivery shaft 74 in accordance with illustrative embodiments of the invention.

The process proceeds to step 414, which asks if there are more sutures to cut? If yes, then the process returns to step 410, which positions the suture 78 in the suture receiving portion 76 of the cutter 64. In some embodiments, the suture cutting device may be removed from the working channel 38 and an endoscopic scissor may be used to cut the suture 78. The process 400 is then repeated substantially as described above until the suture 78 is cut.

When there are no more sutures 78 to cut, the process proceeds to step 416, which removes the suture cutter 64 from the endoscope 18. To remove the suture cutter 64, the suture cutter 64 is retracted back into the delivery shaft 74 and through the insertion tube 22. The inventors determined that removing the suture cutter 64 can be difficult in various embodiments because of interference with the delivery shaft 74. FIGS. 14A-14B schematically show a distal end view of the cutter 64 retracting towards the delivery shaft 74. FIGS. 14A and 14B show two different outcomes of retracting the blade 72 towards the delivery shaft 74.

As shown in FIG. 14A, the cutter 64, particularly the biased blade 72B may interfere with the delivery shaft 74, thereby getting caught on the delivery shaft 74 (e.g., particularly at the point of the maximum height H of the cutter 64). The delivery shaft 74 may undesirably, for example, come to be positioned within the receiving portion 76. This requires further manipulation by the practitioner 14 to remove the shaft 74 from the receiving portion 76, and then to attempt to properly position the cutter 64 within the lumen of the shaft 74, as shown in FIG. 14B. In particular, FIG. 14B shows that there is no interference between the blades 72B and the inner wall 74A of the delivery shaft 74.

In various embodiments, the distal end of the pull wire 60 is bent to assist with blade 72 retraction into the delivery shaft 74. In particular, the bend reduces the likelihood that the blade 72 gets caught on the delivery shaft 72 as it is pulled towards the delivery shaft 74.

FIG. 14C schematically shows a retraction feature 82 of the cutting device 54 in accordance with illustrative embodiments. The retraction feature 82 is configured to position and orient the cutter 64 such that there is minimal or no interference between the one or more blades 72 and the delivery shaft 74 as the cutter 64 is retracted into the delivery shaft 74 (e.g., as shown in FIG. 14B). In some other embodiments, the retraction feature 82 comprises a hypodermic tube 82 (e.g., having a length 83 of about 5 mm to about 9 mm) that is coupled (e.g., welded, glued, integrally formed) to the wire 60 near the distal end of the wire 60 to force the wire 60 near or against the inner wall 74A of the delivery shaft 74. This ensures that adequate space exists for the blade 64 to be retracted inside the delivery shaft 74 (e.g., a catheter). The retraction feature 82 thus minimizes or eliminates interference between the one or blades 72A and delivery shaft 74. To that end, the retraction feature 82 may be sized to be just smaller than the inner diameter of the delivery shaft 74 (to push the wire 60 towards the inner wall of the delivery shaft 74 without causing too much resistance to the movement of the feature 82).

In some embodiments, the pull wire 60 may be coupled to an inner or outer surface of the hypodermic tube 82, such that the pull wire 60 is retained against or next to the inner surface 74A of the delivery shaft 74. The retraction feature 82 may be rigidly fixed to the pull wire 60 such that the cutter 64 is rotationally and movably fixed to the retraction feature 82. Accordingly, when the cutter 64 moves proximally or distally, the retraction feature 82 moves proximally or distally in a corresponding manner. Similarly, when the cutter 64 is rotated, the retraction feature 82 also rotates.

Preferably, the retraction feature 82 is coupled to the pull wire 60 such that the cutter 64 is oriented and positioned to avoid interference with the shaft 74.

FIGS. 15A-15G schematically show a variety of cross-sections of various embodiments having the retraction feature 82. In particular, the cross-section shows the cutter 64 and the delivery shaft 74. It should be understood that the retraction feature 82 is not shown at this cross-section, as the retraction feature 82 may be located proximally of the cutter 64 (e.g., see FIG. 14C).

As an example, a hypothetical plane P1 may be drawn through a maximum diameter of the delivery shaft 74 and an axis of rotation 88 of the cutter 64. A hypothetical plane P2 may also be defined along the maximum height of the cutter 64. An angle α1 is defined between P1 and P2. In various embodiments, certain angles α1 orient the cutter 64 such that there is no interference with the delivery shaft 74 (e.g., shown in FIGS. 15A-15C). However, certain other angles α1 orient the cutter 64 such that there is interference with the delivery shaft 74 (e.g., shown in FIGS. 15D-15G). In some embodiments, the angle α1 is preferably selected such that interference between the maximum height H of the cutter 64 and the shaft 74 is minimized or eliminated.

Although FIGS. 15A-15G refer to various angles with respect to the pull wire 60, it should be understood that the pull wire 60 may be coupled at a variety of points along the cutter 64 (e.g., on a different end of the cutter 64, on an opposite side, etc.). However, illustrative embodiments advantageously couple the wire 60 off-centered from the cutter 64 so that the suture 68 may easily enter the receiving portion 76.

Additionally, the dimensions of the cutter 64, the pull wire 60, and/or the delivery shaft 74 may vary from the examples shown herein. Thus, various embodiments are not limited to the angles described herein. These examples are merely provided to show certain orientations and positions that may be operable using the retraction feature 82. One skilled in the art can determine how to appropriately size and orient the cutter 64, the pull wire 60, and the retraction feature 82 relative to one another in order to ensure that the cutter 64 has limited or no interference with the delivery shaft 74 during retraction. The process 400 then comes to an end.

FIGS. 16-18 schematically show alternative embodiments of the suture cutter 64 in accordance with illustrative embodiments of the invention. FIG. 16 schematically shows the suture cutter 64 having two planar blades 72. The receiving portion 76 may be partially formed from the drive wire 60.

FIG. 17 schematically shows the suture cutter 64 having a single blade 72. The blade edge 70 may face substantially in a proximal direction. Similar to FIG. 16, the receiving portion 76 may be formed from the drive wire 60.

FIG. 18 schematically shows the suture cutter 64 of FIG. 17 having a pre-receiving portion 84. The pre-receiving portion 84 may be formed from the drive wire 60, or may be separately formed. The pre-receiving portion 84 allows the practitioner 14 to initially capture the suture 78 by pushing the cutter 64 in a distal direction (e.g., substantially along the axis A1). Then, as represented by the motion of the arrows, the suture 78 may be brought into the suture receiving portion 76 leading to the blade 72 by aligning the suture 78 with the receiving portion 76 and pulling the cutter 64 in a proximal direction.

It should be apparent to one skilled in the art that illustrative embodiments provide a number of advantages to medical practitioners 14 and the patient 12. Specifically, illustrative embodiments advantageously provide a cutter 64 having a small rigid profile (e.g., length L) that allows for easy movement through an angulated insertion tube 22. Furthermore, illustrative embodiments provide a reduced profile device that does not have moving blades 72. Accordingly, no active control mechanisms for the blades 72 are required (e.g., a control mechanism for rotating the blade(s) around a pin as in conventional scissors). Furthermore, because of the orientation of the cutter 64 relative to the device 54, illustrative embodiments enable cutting of sutures 78 using a pulling motion by the medical practitioner 14. This pulling motion may be made using the same handle 56 that is used to position the cutter 64. The simplified hooking and cutting motion using a single handle 56 advantageously simplifies medical procedures for medical practitioners 14.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Although the above discussion discloses various exemplary embodiments of the invention, it should be apparent that those skilled in the art can make various modifications that will achieve some of the advantages of the invention without departing from the true scope of the invention.

What is claimed is:

1. A method of cutting a suture, the method comprising:
positioning a flexible insertion tube of an endoscope inside of a patient;
moving a passive cutter coupled with a drive wire through a working channel of the flexible insertion tube, the drive wire configured to move the cutter along a central axis of the working channel, the cutter having a proximally-facing suture receiving portion leading to a sharp edge;
extending the cutter out of a delivery shaft;
positioning the sharp edge adjacent to a suture;
cutting the suture by pulling the drive wire proximally; and
retracting the cutter into the delivery shaft, wherein the drive wire is coupled with a retraction feature configured to position and orient the cutter to reduce or prevent interference with the delivery shaft.

2. The method of claim 1, wherein positioning the suture adjacent to the sharp edge comprises:
passing the suture through the suture receiving portion.

3. The method of claim 2, wherein passing the suture through the suture receiving portion comprises:
moving the suture receiving portion distally of a portion of the suture;
aligning the portion of the suture with the suture receiving portion;
moving the suture receiving portion proximally to receive the aligned portion of the suture within the suture receiving portion.

4. The method of claim 1, wherein the cutter has a rigid longitudinal traversal length L of less than about 8 mm.

5. The method of claim 1, further comprising:
positioning the sharp edge adjacent to a second suture; and
cutting the second suture by pulling the cutter proximally.

6. The method of claim 1, wherein the drive wire is angulated near a distal end.

7. The method of claim 1, wherein the cutter has at least one blade forming a suture receiving portion.

8. A method of cutting a suture, the method comprising:
providing:
a drive wire coupled with a cutter having a central axis, wherein the drive wire is offset from the central axis;
the cutter having a first blade with a first sharp edge defining a first cutting direction, the first blade defining a first plane passing through the first blade in the first cutting direction, and a second blade with a second sharp edge defining a second cutting direction, the second blade defining a second plane passing through the second blade in the second cutting direction, the first plane being non-parallel with the second plane, the first blade and the second blade defining an opening;
positioning a suture into the opening;
cutting the suture by pulling the drive wire in a proximal direction.

9. The method of claim 8, wherein the cutter has a rigid longitudinal traversal length L of less than about 4 mm.

10. The method of claim 8, further comprising:
positioning a second suture into the opening; and
cutting the second suture by pulling the drive wire in a proximal direction.

11. The method of claim 8, wherein the flexible insertion tube is angulated near a distal end of the flexible insertion tube.

12. The method of claim 8, wherein a central axis of the cutter diverges from a central axis of the working channel when the cutter is extended out of the delivery shaft.

13. The method of claim 8, wherein the drive wire is configured to bend outside of the delivery shaft.

14. The method of claim 8, further comprising retracting the cutter into a delivery shaft, wherein the drive wire is coupled with a retraction feature configured to position and orient the cutter to reduce or prevent interference with the delivery shaft.

15. The method of claim 14, wherein the retraction feature is a hypodermic tube.

16. The method of claim 8, further comprising providing a retraction feature configured to position and orient the cutter to reduce or prevent interference with a delivery shaft.

17. The method of claim 8, wherein the first blade and the second blade are non-moving.

\* \* \* \* \*